United States Patent
Toner et al.

(10) Patent No.: US 7,445,792 B2
(45) Date of Patent: Nov. 4, 2008

(54) MEDICAL DEVICE HAVING A HYDRATION INHIBITOR

(75) Inventors: John L. Toner, Libertyville, IL (US); Keith R. Cromack, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 874 days.

(21) Appl. No.: 10/796,243

(22) Filed: Mar. 9, 2004

(65) Prior Publication Data

US 2004/0180039 A1 Sep. 16, 2004

Related U.S. Application Data

(60) Provisional application No. 60/453,555, filed on Mar. 10, 2003.

(51) Int. Cl.
*A61F 2/00* (2006.01)
*A61F 2/06* (2006.01)

(52) U.S. Cl. ................. 424/423; 623/1.15; 623/1.46

(58) Field of Classification Search ............. 424/422, 424/93.2, 426, 423; 623/1.15, 1.46
See application file for complete search history.

(56) References Cited

U.S. PATENT DOCUMENTS

| | | | |
|---|---|---|---|
| 4,916,193 A | 4/1990 | Tang et al. | |
| 4,994,071 A | 2/1991 | MacGregor | |
| 5,092,877 A | 3/1992 | Pinchuk | |
| 5,163,952 A | 11/1992 | Froix | |
| 5,304,121 A | 4/1994 | Sahatjian | |
| 5,355,832 A | 10/1994 | Loh et al. | |
| 5,447,724 A | 9/1995 | Helmus et al. | |
| 5,447,799 A | 9/1995 | Loh et al. | |
| 5,464,650 A | 11/1995 | Berg et al. | |
| 5,605,696 A | 2/1997 | Eury et al. | |
| 5,624,411 A | 4/1997 | Tuch | |
| 5,705,583 A | 1/1998 | Bowers et al. | |
| 5,722,984 A * | 3/1998 | Fischell et al. | 606/198 |
| 5,869,079 A | 2/1999 | Wong et al. | |
| 6,015,815 A | 1/2000 | Mollison | |
| 6,040,415 A * | 3/2000 | Arimori et al. | 528/71 |
| 6,083,257 A | 7/2000 | Taylor et al. | |
| 6,090,901 A | 7/2000 | Bowers et al. | |

(Continued)

FOREIGN PATENT DOCUMENTS

EP 0 568 310 3/1996

(Continued)

OTHER PUBLICATIONS

U.S. Appl. No. 09/950,307.

(Continued)

*Primary Examiner*—Sharon E. Kennedy
(74) *Attorney, Agent, or Firm*—Squire, Sanders & Dempsey L.L.P.

(57) ABSTRACT

A medical device having a hydration inhibitor for controlled delivery of a beneficial agent and methods of manufacturing of the same. The medical device includes an interventional component loaded with a beneficial agent having a first Log P value, the beneficial agent being associated with a hydration inhibitor to control the elution rate of at least part of the beneficial agent, the hydration inhibitor having a second Log P value which is greater than the first Log P value.

59 Claims, 12 Drawing Sheets

U.S. PATENT DOCUMENTS

| | | |
|---|---|---|
| 6,284,305 B1 | 9/2001 | Ding et al. |
| 6,299,604 B1 | 10/2001 | Ragheb |
| 6,329,386 B1 | 12/2001 | Mollison |
| 6,358,556 B1 | 3/2002 | Ding et al. |
| 6,419,692 B1 | 7/2002 | Yang et al. |
| 6,872,225 B1 * | 3/2005 | Rowan et al. .............. 623/1.15 |

FOREIGN PATENT DOCUMENTS

| | | |
|---|---|---|
| WO | 98/36784 | 8/1998 |
| WO | 00/21584 | 4/2000 |
| WO | 01/87372 A1 | 11/2001 |

OTHER PUBLICATIONS

U.S. Appl. No. 60/424,576.
U.S. Appl. No. 60/424,577.
U.S. Appl. No. 60/424,607.
PCT Patent Application Serial No. PCT/US02/28776.
McGraw-Hill Encyclopedia of Chemistry, 2nd ed., 535-539 (1993).
Solubility Data Series, "Hydrocarbons with Water and Seawater, Part II: Hydrocarbons $C_8$ to $C_{36}$", vol. 38, Pergamon Press (1985).
Osol, A., et al., *Remington's Pharm. Sci.*, 16th ed.:256-7 & 294-5 (1980).
Pinsuwan, S., et al., "Correlation of Octanol/Water Solubility Ratios and Partition Coefficients", *J. Chem. Eng. Data*, 40:623-626 (1995).
Sangster, J., *J. Phys. Chem. Ref. Data*, 18(3):1111-1229 (1989).
Shiu, W.Y., & Mackay, D., "A Critical Review of Aqueous Solubilities, Vapor Pressures, Henry's Law Constants, and Octanol-Water Partition Coeffients of the Polychlorinated Biphenyls", *J. Phys. Chem. Ref. Data*, 16(2):911-929 (1986).
M. Helmus et al., "Medical Device Design—A Systems Approach: Central Venous Catheters", 22nd Intern'l SAMPE Tech. Conf., 113-126 (1990).
T. Higuchi and V. Stella, Eds., "Pro-drugs as Novel Drug Delivery Systems", A.C.S. Symposium Series 14, 1975 (Table of Contents only).
M. Miller et al., "Aqueous Solubilities, Octanol/Water Partition Coefficients, and Entropies of Melting of Chlorinated Benzenes and Biphenyls", J. Chem. Eng. Data, 29: 184-190 (1984).

* cited by examiner

BiodivYsio PC-coated Stent
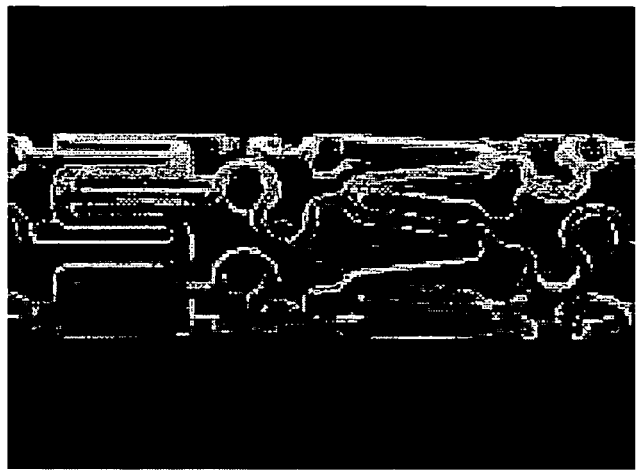
Fig 2
**Vessel Segments
Mayo Clinic Study in Domestic Swine**
Polymer Only      Polymer plus Drug
Fig 3A      Fig 3B
Fig 3

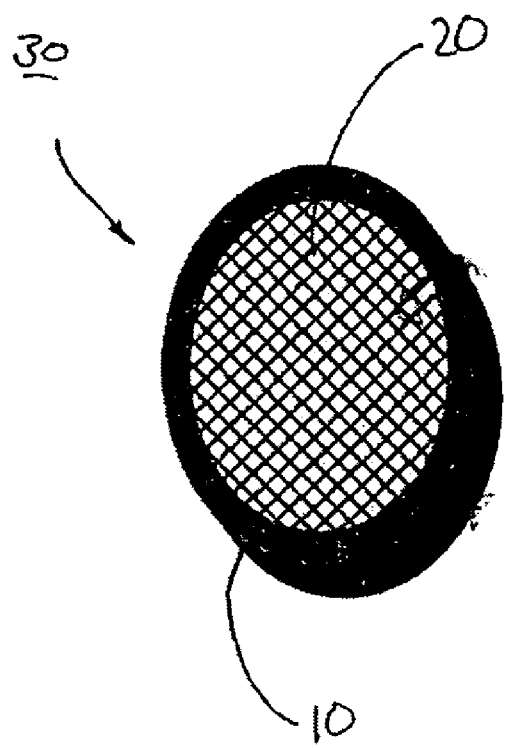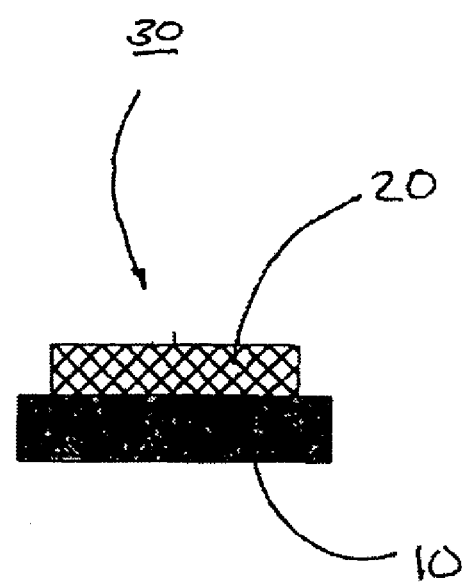
FIG. 9A
FIG. 9B

MEDICAL DEVICE HAVING A HYDRATION INHIBITOR

This application claims priority to the provisional application Ser. No. 60/453,555 filed on Mar. 10, 2003

BACKGROUND OF THE INVENTION

1. Field of the Invention

The present invention relates to a medical device for controlled delivery of a beneficial agent having an interventional component loaded with a beneficial agent and the beneficial agent being associated with a hydration inhibitor that controls delivery of the beneficial agent from the interventional component. The present invention also relates to a method of manufacturing the medical device.

2. Description of Related Art

In surgical or other related invasive medicinal procedures, the insertion of a medical device having an interventional component such as stent devices in blood vessels, urinary tracts or other difficult to access places for the purpose of preventing restenosis, providing vessel or lumen wall support or reinforcement and for other therapeutic or restorative functions has become a common form of long-term treatment. Typically, such intervention components are applied to a location of interest utilizing a vascular catheter, or similar transluminal device, to carry the stent to the location of interest where it is thereafter released to expand or be expanded in situ. These devices are generally designed as permanent implants which may become incorporated in the vascular or other tissue that they contact at implantation.

Implanted interventional components such as stents have also been used to carry medicinal agents, such as thrombolytic agents. U.S. Pat. No. 5,163,952 to Froix discloses a thermal memoried expanding plastic stent device that can be formulated to carry a medicinal agent by utilizing the material of the stent itself as an inert polymeric drug carrier.

Drug elution rates from a drug-loaded coating containing a hydrophilic (or lipophobic) drug are usually very fast initially when the coated device contacts body fluid or blood. Thus, an ongoing problem for drug delivery stents is achieving therapeutic drug concentrations at a target site within the body with minimal losses and systemic side effects. One technique to reduce the so-called burst effect is to add a membrane containing porosigen over the coating layer containing the biologically active material, as described for example in U.S. Pat. Nos. 5,605,696 and 5,447,724. Polymers are also used on stents as drug release coatings, as taught for example in U.S. Pat. No. 6,419,692. U.S. Pat. No. 6,284,305 describes elastomer coated implants in which the elastomer overcoat to control release of biologically active agent from an undercoat applied to a stent. U.S. Pat. No. 5,624,411 discloses a porous polymer on a stent to control the administration of a drug. WO 0187372 describes a stent coated with a polymer loaded with a combination of drugs, such as rapamycin and dexamethasone. Pinchuk, in U.S. Pat. No. 5,092,877, discloses a stent of a polymeric material that may be employed with a coating associated with the delivery of drugs. Other patents which are directed to devices of the class utilizing bio-degradable or bio-sorbable polymers include Tang et al, U.S. Pat. No. 4,916,193 and MacGregor, U.S. Pat. No. 4,994,071. Sahatjian in U.S. Pat. No. 5,304,121, discloses a coating applied to a stent consisting of a hydrogel polymer and a preselected drug; possible drugs include cell growth inhibitors and heparin. A further method of making a coated intravascular stent carrying a therapeutic material in which a polymer coating is dissolved in a solvent and the therapeutic material dispersed in the solvent and the solvent thereafter evaporated is described in Berg et al, U.S. Pat. No. 5,464,650.

An article by Michael N. Helmus entitled "Medical Device Design—A Systems Approach: Central Venous Catheters", 22nd International Society for the Advancement of Material and Process Engineering Technical Conference (1990) relates to polymer/drug/membrane systems for releasing heparin. Those polymer/drug/membrane systems require two distinct layers to function. Ding et al., U.S. Pat. No. 6,358,556 described a process for coating a stent prosthesis using a biostable hydrophobic elastomer in which biologically active species are incorporated within a cured coating. In these coatings, the amount of polymer is relatively high, for example about 70% of the drug-loaded coating.

Thus, there remains a need for improved controlled delivery of a hydrophilic beneficial agent from a medical device, wherein the medical device reduces the burst effect and allows prolonged delivery of the beneficial agent without the side effects associated with some hydrophobic coatings. Also, there exist a need for a medical device with improved control of systemic release of two or more beneficial agents systematically. Further, a need exists for a medical device that is capable of releasing a beneficial agent immediately or soon after delivery followed by the controlled delivery of the same or other beneficial agents. The advantages of the present invention satisfy the aforementioned needs. Other advantages of the present invention will become apparent to those stilled in the art upon familiarization with the specification and appended claims.

SUMMARY OF THE INVENTION

The purpose and advantages of the present invention will be set forth in and apparent from the description that follows, as well as will be learned by practice of the invention.

Additional advantages of the invention will be realized and attained by the devices and methods particularly pointed out in the written description and claims hereof, as well as from the appended drawings.

To achieve these and other advantages and in accordance with the purpose of the invention, as embodied and broadly described, the invention includes a medical device having an interventional component at least partially loaded with a beneficial agent and the beneficial agent being associated with a hydration inhibitor to control delivery of the beneficial agent from the interventional component once deployed in a patient. The device comprises an interventional component to be deployed in a patient, a beneficial agent to be delivered from the interventional component, the beneficial agent loaded on at least a portion of the interventional component and having a first Log P value; and an effective amount of a hydration inhibitor associated with the beneficial agent to control delivery of the beneficial agent from the interventional component, the hydration inhibitor having a second Log P value, the second Log P value being greater than the first Log P value. Preferably the first Log P value is at least about 0.1 unit less than the second Log P value and more preferably the first Log P value is at least about 0.5 units less than the second Log P value.

In another aspect of the invention, the medical device has a layer of polymeric material on at least at portion of a surface of the interventional component, wherein a polymeric material base layer is loaded with the beneficial agent and a hydration inhibitor is associated with the beneficial agent. Preferably the hydration inhibitor controls the delivery of the beneficial agent from the layer of polymeric material.

In a further aspect of the invention, the beneficial agent is selected from a group consisting of antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, anti-allergic substances, viral vectors, nucleic acids, monoclonal antibodies, antisense compounds, oligionucleotides, cell permeation enhancers, pro-drugs and combinations thereof. The beneficial agent can also be selected from the group of specific agents including indomethacin, phenyl salicylate, B-estradiol, vinblastine, ABT-627, testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof.

Alternatively, the beneficial agent selected can be a nucleic acid that encodes a pharmaceutically useful peptide or an anti-sense oligo-nucleotide used to control a gene of interest in a cell of the patient.

Generally, the hydration inhibitor is selected from the group of beneficial agents, polymeric materials, markers, additives, and combinations thereof. Preferably, when the hydration inhibitor is a second beneficial agent it is selected from a group consisting of antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, radiopaque agents markers and combinations thereof, wherein the second beneficial agent has a Log P value that is greater than the first beneficial agent to control delivery of the first beneficial agent. The second beneficial agent can also be selected from a group consisting of paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, ABT-578, ABT-627 and analogs, derivatives, or combinations thereof.

The beneficial agent is preferably associated with the hydration inhibitor as a mixture. Alternatively, when the hydration inhibitor is a second beneficial agent, the second beneficial agent can be associated with the first beneficial agent as a layer of the second beneficial agent at least partially covering the first beneficial agent. The medical device can further include an outer layer of a third beneficial agent, the third beneficial agent having a third Log P value. Preferably, the third Log P value is less than the second Log P value and more preferably the third beneficial agent is the same as the first beneficial agent.

In a further aspect of the invention, the hydration inhibitor is an additive selected from a group consisting of nitrophenyl octyl ether, bisethylhexyl sebacate, diisododecylphthalate, N-methylpyrrolidone, and combinations thereof.

In another aspect of the invention the hydration inhibitor is a polymeric material selected from a group consisting of phosphorylcholine, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly (iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane, polycarbonate urethanes, polyethylene, polyethylene terapthalate, ethylene vinyl acetate, ethylene vinyl alcohol, silicone polysiloxanes, substituted polysiloxanes, polyethylene oxide, polybutylene tereptphalate-co-PEG, PCL-co-PEG, PLA-co-PEG, polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or combination thereof. Preferably the polymeric material has a zwitterionic pendant group.

In yet another aspect of the invention, a method is provided of manufacturing a medical device, the method comprising the steps of: providing an interventional component to be deployed in a patient; loading a beneficial agent on the interventional component for delivery therefrom, the beneficial agent having a first Log P value; and associating an effective amount of a hydration inhibitor with the beneficial agent to control delivery of the beneficial agent from the interventional component, the hydration inhibitor having a second Log P value, the second Log P value being greater than the first Log P value.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

FIG. 2 is a side view in elevation showing a PC-coated (phosphorylcholine-coated) stent suitable for use in this invention.

FIG. 3A is a cross-sectional view of a vessel segment in which was placed a stent coated with a polymer only.

FIG. 3B is a cross-sectional view of a vessel segment in which was placed a stent coated with a polymer plus drug.

FIG. 9A is a top view of a drug-loaded coupon according to the present invention.

FIG. 9B is a side view of a drug-loaded coupon according to the present invention.

DETAILED DESCRIPTION OF THE PREFERRED EMBODIMENT

Figure 1:
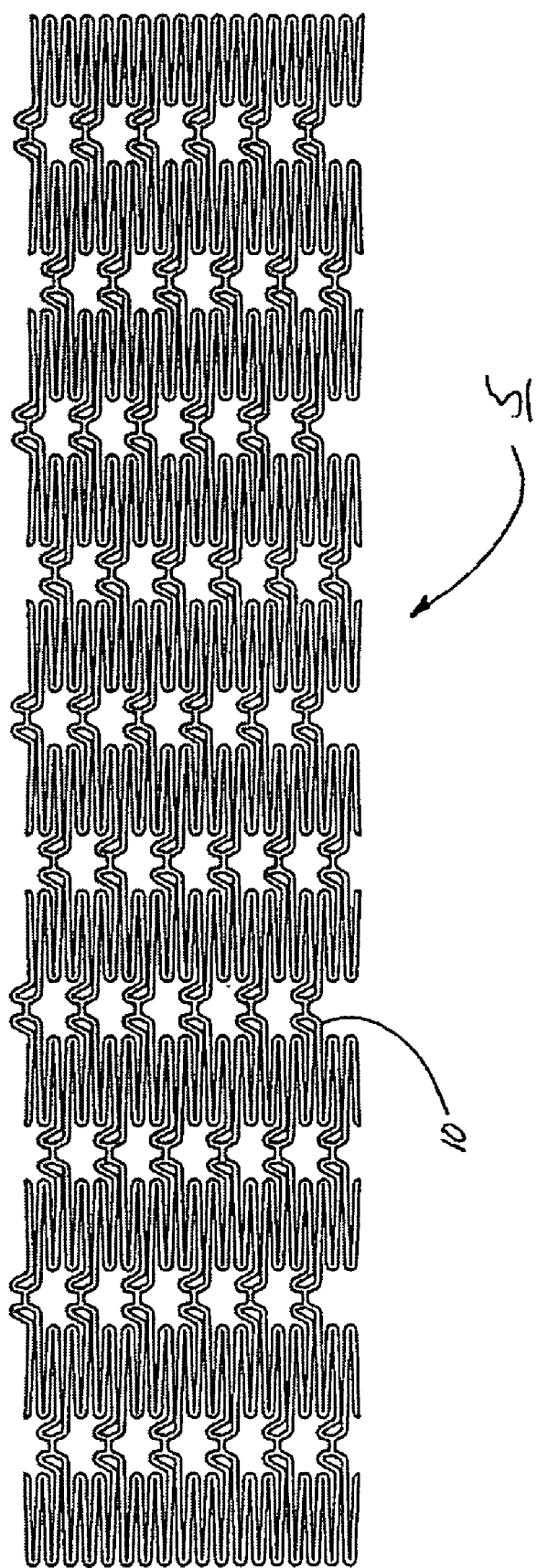
FIG. 1 is a side view of an exemplary interventional device (stent) according to the present invention.
Figure 4:
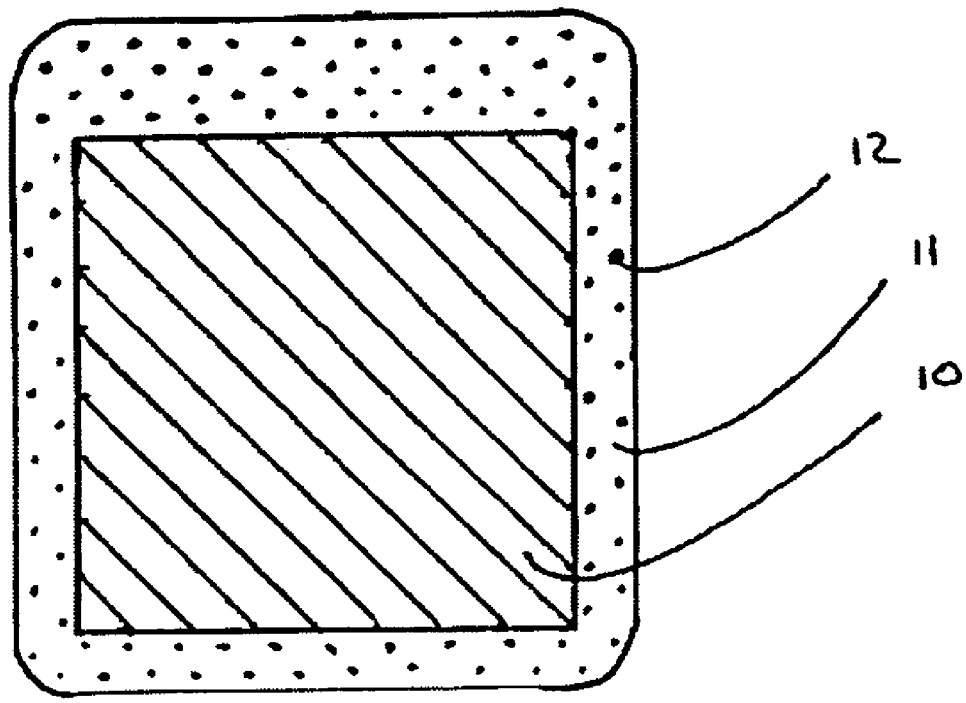
FIG. 4 is a cross-sectional view of a stent strut having a layer of a beneficial agent and hydration inhibitor in mixture.

Reference will now be made in detail to the present preferred embodiments of the medical device having a hydration inhibitor for controlled delivery of a beneficial agent and method of making the device. The method of the present invention will be described in conjunction with the medical device. Wherever possible, the same reference characters will be used throughout the drawings to refer to the same or like parts.

In accordance with the present invention, a medical device is provided having an interventional component that is loaded with a beneficial agent that is associated with a hydration inhibitor to control the delivery of the beneficial agent in a patient. As used herein "medical device" refers broadly to any device that is deployed in a patient. In a preferred embodiment, the present invention is directed to a medical device having controlled delivery of a beneficial agent for the treatment and prevention of cardio, vascular or other intraluminal diseases. Preferably the medical device is suitable for intraluminal delivery or implantation.

As is known in the art, such devices can comprise one or more interventional components. For purposes of illustration and not limitation, examples of such medical devices include stents, grafts, stent-grafts, valves, filters, coils, staples, sutures, guidewires, catheters, catheter balloons, and the like. In a preferred embodiment the interventional component is an interventional component having a first cross-sectional dimension for the purpose of delivery and a second cross-sectional dimension after deployment and can be deployed by known mechanical techniques such as balloon expansion deployment techniques, or by electrical or thermal actuation, or self-expansion deployment techniques, as well known in the art. For example, and as embodied herein, representative embodiments of a stent, stent-graft or similar interventional component are disclosed in U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, are all incorporated herein by reference. It is recognized, however, that the interventional component can be any type of implantable or deployable interventional component capable of being loaded with beneficial agent.

The interventional component can be in an expanded or unexpanded state during the loading of beneficial agent. The underlying structure of the interventional component can be virtually any design and the interventional component can be composed any suitable material such as, but not limited to, stainless steel, "MP35N," "MP20N," elastinite (Nitinol), tantalum, nickel-titanium alloy, platinum-iridium alloy, chromium-cobalt alloy, gold, magnesium, polymer, ceramic, tissue, or combinations thereof. "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. Similarly, the interventional component can be made from bioabsorbable or biostable polymers. In some embodiments, the surface of the interventional component can be porous or impervious, or include one or more reservoirs or cavities formed therein for purpose of retaining beneficial agent therein as is known in the art.

The interventional component can be fabricated utilizing any number of methods known in the art. For example, the interventional component can be fabricated from a hollow or formed tube that is machined using lasers, electric discharge milling, chemical etching or other known techniques. Alternatively, the interventional component can be fabricated from a sheet or formed of a wire or filament construction as known in the art.

In accordance with the present invention, the interventional component is loaded with beneficial agent to be delivered therefrom when deployed within the patient. "Beneficial agent" as used herein, generally refers to any compound, mixture of compounds, or composition of matter consisting of a compound, which produces a beneficial or useful result in a patient. The beneficial agent has a first Log P value.

The symbol "P" of "Log P" is the calculated partition coefficient of a chemical substance, which is a measure of the way in which a compound will partition itself between the octanol and water phases in the two-phase octanol-water system, and thus an indicator of certain types of biological activity. Specifically, P is the ratio of the concentration (in moles per liter) of the compound in the octanol phase to that in the water phase at infinite dilution. The solubility is usually expressed as base 10 logarithm of the partition coefficient, Log P. Log P and methods for calculating it are well known to those skilled in the art. The Log P value can be calculated by the method described in (Hansch C. and Leo A. "Substituent Constants for Correlation Analysis in Chemistry and Biology" Wiley, N.Y., 1979). The characteristic of being "relatively less hydrophilic" or "relatively more hydrophilic" as disclosed herein is determined according to the Log P value calculations. A discussion of methods of measurement and accuracy considerations for logP is found in Sangster, J., J. Phys. Chem. Ref. Data, 18, 1111, 1989, incorporated herein by reference. Log P values can also be calculated by the method described in Hansch C. and Leo A. "Substituent Constants for Correlation Analysis in Chemistry and Biology" Wiley, N.Y., 1979. Other discussions of Log P may be found in the following documents, incorporated herein by reference: Mackay, D., Shiu, W. Y., and Ma, K. C., Illustrated Handbook of Physical-Chemical Properties and Environmental Fate for Organic Chemicals, Lewis Publishers/CRC Press, Boca Raton, Fla., 1992; Shiu, W. Y., and Mackay, D., J. Phys. Chem. Ref. Data, 15, 911, 1986; Pinsuwan, S., Li, L., and Yalkowsky, S. H., J. Chem. Eng. Data, 40, 623, 1995; Solubility Data Series, International Union of Pure and Applied Chemistry, Vol. 20, Pergamon Press, Oxford, 1985; Solubility Data Series, International Union of Pure and Applied Chemistry, Vol. 38, Pergamon Press, Oxford, 1985; Miller, M. M., Ghodbane, S., Wasik, S. P., Tewari, Y. B., and Martire, D. E., J. Chem. Eng. Data, 29, 184, 1984.

Log P is a widely used parameter for correlating biological effects of organic substances. It is a property of the two-phase system in which water and 1-octanol are in equilibrium at a fixed temperature and the substance is distributed between the water-rich and octanol-rich phases.

Generally, the greater the Log P value of a compound or agent, the less hydrophilic the compound or agent. It also has been determined that a compound or agent having a greater Log P value (i.e., a "relatively less hydrophilic agent") will inhibit hydration of the a second compound or agent having a lower Log P value (i.e., a "relatively more hydrophilic agent"). Thus, and in accordance with the present invention, a relatively less hydrophilic agent can be used as a hydration inhibitor for a relatively more hydrophilic beneficial agent, which is to be delivered from an interventional component as a beneficial agent, wherein the hydration inhibitor has a Log P value that is greater than the Log P value of the beneficial agent. Preferably the Log P value of the hydration inhibitor is at least 0.1 units greater than the beneficial agent and more preferably at least 0.5 units greater than the beneficial agent. Particularly, and in a preferred embodiment of the present invention, the Log P value of the beneficial agent is less than 4.5 units, and more preferably it is less than 3.0 units. See "CRC Handbook of Chemistry and Physics," 3rd Electronic Edition, 2000. However, it is possible for a compound to serve as a hydration inhibitor of the elution of a given beneficial agent according to the present invention when the beneficial agent's Log P value is less than that of the given hydration inhibitor.

Although those skilled in the art are familiar with Log P values and the well-known methods for calculation thereof, for purpose of illustration, and not limitation, Table 1 provides a representative summary of Log P values for several suitable beneficial agents for use with the present invention.

TABLE 1

| Beneficial Agent | Log P Values |
| --- | --- |
| Probucol | >8 |
| Linolenic acid | >6 |
| Linoleic acid | >6 |
| Stearic acid | >6 |
| Oleic acid | >6 |
| Paclitaxel | >5 |
| Danazol | 4.5 |
| Rapamycin | >4.5 |
| ABT-578 | >4.5 |
| Tacrolimus | >4.5 |
| Fenofibrate | >4.5 |
| Indomethacin | 4.3 |
| Phenyl salicylate | 4.1 |
| B-estradiol | 4 |
| Vinblastine | 3.6 |
| ABT-627 | 3.4 |
| Testosterone | 3.3 |
| Progesterone | 3.2 |
| Paclitaxel | >3 |
| Cyclosporin A | 2.9 |
| Vincristine | 2.6 |
| Carvedilol | 1.97 |
| Dexamethasone | ~1.9-2.2 |
| Vindesine | 1.3 |

TABLE 1-continued

| Beneficial Agent | Log P Values |
| --- | --- |
| Dipyridamole | 1-2 |
| Methotrexate | −1.85 |

A variety of suitable beneficial agents for delivery of an interventional component are well known. For example, and not limitation, various suitable beneficial agents having a Log P value include markers, such as a radiopaque dyes or particles, drugs, such as pharmaceutical and therapeutic agents, and inorganic or organic drugs without limitation. The agent or drug can be in various forms, components of molecular complexes, pharmacologically-acceptable salts such as hydrochloride, hydrobromide, sulfate, phosphate, nitrate, borate, acetate, maleate, tartrate and salicylate.

For purposes of illustration and not limitation, the drug or agent includes antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, pro-drugs and combinations thereof. Other beneficial agents include but are not limited to nucleic acids that encode a pharmaceutically useful peptide or an anti-sense oligo-nucleotide used to control a gene of interest in a cell.

Examples of specific beneficial agents of interest include indomethacin, phenyl salicylate, β-estradiol, vinblastine, ABT-627 (atrasentan), testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof. The term "prodrug," as used herein, refers to compounds, which are transformed in vivo to the parent compound of the above formula, for example, by hydrolysis in blood. A thorough discussion is provided by T. Higuchi and V. Stella, "Pro-drugs as Novel Delivery systems," Vol. 14 of the A. C. S. Symposium Series, and in Edward B. Roche, ed., "Bioreversible Carriers in Drug Design," American Pharmaceutical Association and Pergamon Press, 1987, both of which are incorporated herein by reference.

Beneficial agents can have various art known forms such as solutions, dispersions, pastes, particles, granules, emulsions, suspensions and powders. The beneficial agent typically is associated with the hydration inhibitor as a mixture, although can be associated as a separate application, such as an overcoat or layer when a beneficial agent is used as the hydration inhibitor as disclosed further below.

While the foregoing beneficial agents are well known for their preventive and treatment properties, the substances or agents are provided by way of example and not limitation. Further, other beneficial agents with suitable Log P values that are currently available or can be developed are equally applicable for use with the present invention.

Further in accordance with the present invention, an effective amount of hydration inhibitor is associated with the beneficial agent to be delivered from the interventional component so as to control delivery therefrom. The term "hydration inhibitor" as used herein refers to a suitable compound or agent or the like having a Log P value greater than that of the beneficial agent. The hydration inhibitor is thus relatively less hydrophilic than the beneficial agent, and controls delivery of the beneficial agent by retarding, inhibiting or otherwise sustaining the rate in which the beneficial agent would be delivered from the interventional component without the hydration inhibitor associated therewith. Delivery of the beneficial agent from the interventional component occurs by any of a variety of know mechanisms, such as elution, diffusion, dissolution, permeation or other transport mechanisms in vivo.

Generally, "effective amount" of hydration inhibitor refers to an amount sufficient to inhibit hydration of the beneficial agent to be delivered from the interventional component. For example, it is well known to determine hydration as a measure of optical contact angle, wherein a contact angle of about 30° is indicative of a hydrophilic compound and a contact angle of greater than about 50° is indicative of a hydrophobic compound. Optical contact angle and methods for calculating it are well known to those skilled in the art using standard evaluation methods and is disclosed in "McGraw-Hill Encyclopedia of Chemistry," 538 (Sybil P. Parker, 2nd ed. 1993) and "Remington's Pharmaceutical Sciences," 256-7 and 294-5 (Arthur Osol et al. eds., 16th ed. 1980), herein incorporated by reference. As such, an effective amount of hydration inhibitor is recognized to be a sufficient amount to shift the optical contact angle of the beneficial agent in association with the hydration inhibitor to at least about 50° and more preferably to at least about 70°.

For purposes of illustration and not limitation, the hydration inhibitor includes beneficial agents (including markers), polymeric materials, additives and combinations thereof. When a second "beneficial agent" is used as the hydration inhibitor, the Log P value of the second beneficial agent must be greater than the Log P value of the first beneficial agent. Examples of such beneficial agent hydration inhibitors include antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, radiopaque agents markers and combinations thereof.

Non-limiting examples of specific beneficial agent useful as hydration inhibitors include paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, ABT-578, ABT-627 and analogs, derivatives, or combinations thereof. The following is the chemical structure of ABT-627

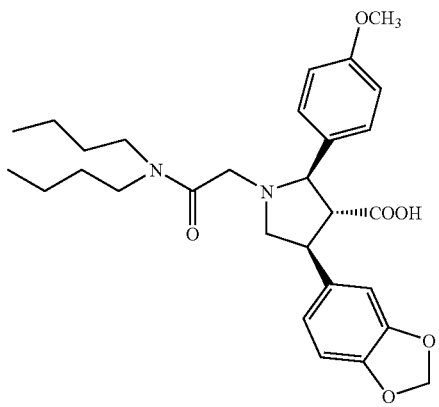

and the chemical structure of ABT-578 is

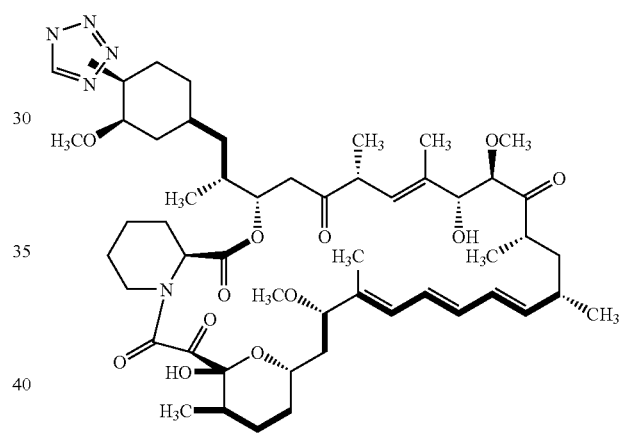

A detailed discussion of ABT-627 (atrasentan) is available in PCT/US02/28776, filed Sep. 10, 2002, and ABT-578 in U.S. Pat. Nos. 6,015,815 and 6,329,386, the disclosure of each is incorporated by reference herein.

Although the hydration inhibitor is preferably associated with the beneficial agent as a mixture, in an alternative embodiment, wherein the hydration inhibitor is a second beneficial agent, the hydration inhibitor can be associated as an overcoat or encapsulating layer covering at least a portion of the first beneficial agent.

Polymeric materials suitable as hydration inhibitors are typically a product of a polymerization reaction inclusive of homopolymers, copolymers, terpolymers, etc., whether natural or synthetic, including random, alternating, block, graft, branched, cross-linked, blends, compositions of blends and variations thereof. The polymer can be in true solution, saturated, or suspended as particles or supersaturated in the beneficial agent. The polymer is biocompatible, and can be biodegradable.

Examples of such polymeric materials include phosphorylcholine, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane, polycarbonate urethanes, polyethylene, polyethylene terapthalate, ethylene vinyl acetate, ethylene vinyl alcohol, silicone polysiloxanes, substituted polysiloxanes, polyethylene oxide, polybutylene terepthalate-co-PEG, PCL-co-PEG, PLA-co-PEG, polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or combination thereof.

In a preferred embodiment, the polymeric material has a zwitterionic pendant group. Preferably, the polymer is phosphorylcholine disclosed in U.S. Pat. Nos. 5,705,583 and 6,090,901 to Bowers et al. and U.S. Pat. No. 6,083,257 to Taylor et al, the disclosure of each is incorporated in entirety by reference herewith.

As noted above, the beneficial agent can include a beneficial agent and polymer mixture. In accordance with the method of the invention, the first beneficial agent can correspond to a beneficial agent-polymer mixture having a concentration of polymer to effect the delivery rate of the particular beneficial agent in the beneficial agent mixture. For example, a beneficial agent-polymer mixture having a higher concentration of polymer would have a slower delivery rate of the beneficial agent within the lumen. In contrast, a beneficial agent-polymer mixture having a lower concentration of polymer would cause a more rapid delivery rate of the beneficial agent. The delivery rate is also effected by the difference between the Log P value of the hydration inhibitor and the Log P value of the beneficial agent. For example, generally the greater the difference between the Log P values the greater the retardation of the beneficial agent's delivery rate as compared to the beneficial agent without hydration inhibitor.

Examples of additives suitable as hydration inhibitors include plasticizers, small molecules and oils. Additives are drawn from compounds, polymers, and mixtures without restriction. When used with an interventional device having a polymer coating, an additive is often capable of dispersing through the polymer coating and rendering it effectively more difficult to hydrate as empirically defined as an increase in swelling time in contact with aqueous solution vs. control polymer coating.

Specific non-limiting examples of additives include nitrophenyl octyl ether, bisethylhexyl sebacate, diisododecylphthalate, N-methylpyrrolidone, linolenic acid, linoleic acid, stearic acid, oleic acid, and combinations thereof.

The hydration inhibitor can be associated with the beneficial agent in any of a variety of conventional techniques. As embodied herein, and as previously noted, it is preferable to associate the hydration inhibitor with the beneficial agent as a mixture of the compounds. The mixture can be accomplished by a physical combination in a variety of forms, including solution, suspension, solid interspersion, vapor phase deposition or any physical combination.

An additional aspect of the invention includes the use of a base layer of polymer material to facilitate loading of a beneficial agent on the interventional component. This aspect of the invention is of particular importance if the beneficial agent is difficult or unsuitable for loading alone or in combination with a suitable binder or the like.

When a coating is used in the present invention, the coating can comprise any polymeric material in which the therapeutic agent, i.e., the drug, is substantially soluble. The purpose of the coating is to serve as a controlled release vehicle for the therapeutic agent or as a reservoir for a therapeutic agent to be delivered at the site of a lesion. The coating can be polymeric and can further be hydrophilic, hydrophobic, biodegradable, or non-biodegradable. The material for the polymeric coating can be selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. Coatings prepared from polymeric dispersions such as polyurethane dispersions (BAYHYDROL, etc.) and acrylic acid latex dispersions can also be used with the therapeutic agents of the present invention.

Biodegradable polymers that can be used in this invention include polymers such as poly(L-lactic acid), poly(DL-lactic acid), polycaprolactone, poly(hydroxy butyrate), polyglycolide, poly(diaxanone), poly(hydroxy valerate), polyorthoester; copolymers such as poly (lactide-co-glycolide), polyhydroxy (butyrate-co-valerate), polyglycolide-co-trimethylene carbonate; polyanhydrides; polyphosphoester; polyphosphoester-urethane; polyamino acids; polycyanoacrylates; biomolecules such as fibrin, fibrinogen, cellulose, starch, collagen and hyaluronic acid; and mixtures of the foregoing. Biostable materials that are suitable for use in this invention include polymers such as polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof; and mixtures and copolymers of the foregoing.

A medical devices to which coatings are applied according to the invention can be pretreated to prepare the surfaces for application of coatings. For example, stainless steel stents may be electropolished prior to coating (e.g., undercoat) application. Useful medical devices can be formed from NITINOL alloy, TRIPLEX (stainless steel/tantalum/stainless steel layer) or cobalt chromium alloy. The coatings optionally include a polymeric material, e.g., phosphorylcholine, polycaprolactone, poly-D,L-lactic acid, poly-L-lactic acid, poly (lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene® brand poly-para-xylylene (available from SCSCookson Industries, Indianapolis, Ind.), Paryl AST™ brand biocompatible dielectric polymer (U.S. Pat. Nos. 5,355,832 and 5,447,799, commercially available from AST Products of Billerica, Mass.); polyurethane, polycarbonate urethanes, polyethylene, polyethylene terephthalate, ethylene vinyl acetate, ethylene vinyl alcohol, silicone polysiloxanes, substituted polysiloxanes, polyethylene oxide, polybutylene terephthalate-co-PEG, PCL-co-PEG (i.e., polycaprolactone co-polyethylene glycol), PLA-co-PEG (i.e., polylactic acid-co-polyethylene glycol), polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or blends thereof (e.g., PLLA-phosphorylcholine).

In any of the embodiments disclosed herein, a porous or biodegradable membrane or layer made of biocompatible materials may be coated over the beneficial agent for sustained release thereof, if desired. Alternatively, a suitable base coating capable of retaining beneficial agent therein can be applied uniformly over the surface of the prosthesis, and then selected portions of the base coating can be loaded with the beneficial agent in accordance with the invention. A greater amount of beneficial agent can be loaded over a unit surface area intended to have a greater local areal density and a lower amount of beneficial agent can be loaded over a unit surface area intended to have a lower local areal density.

In yet another embodiment of the present invention, the beneficial agent may be applied directly to the surface of the prosthesis. Generally a binder or similar component may be used to ensure sufficient adhesion. For example, this coating technique may include admixing the beneficial agent with a suitable binder or polymer to form a coating mixture, which is then coated onto the surface of the prosthesis. The coating mixture would be prepared in higher or lower concentrations of beneficial agent as desired, and then applied to selected portions of the prosthesis appropriately.

As noted above, the beneficial agent may be applied to the interventional component in a polymer, such as drug/polymer mixture. Preferably, the amount of polymer in the mixture is small compared to the amount of drug. For example, the polymer can be about 10% of the amount of drug. In these embodiments, the polymer facilitates processing or loading or enhances retention of the drug on the interventional device, but is in an amount that is not effective to substantially inhibit the hydration of the drug. The presence of the hydration inhibitor of suitable Log P as set forth above has the greater influence on delivery of the drug in this circumstance.

In accordance with some embodiments of the invention, the first and second beneficial agents may correspond to drug-polymer mixtures having different concentrations of polymer to effect different release rates of the particular drug in each beneficial agent. For example, the drug-polymer mixture having a higher concentration of polymer would have a slower release of the drug within the lumen. In contrast, the drug-polymer mixture having a lower concentration of polymer would cause a more rapid release of the drug. Alternatively, rather than providing drug-polymer mixtures having different polymer concentrations to provide different release rates, it is also possible to dispense beneficial agents within different polymers or other binders, wherein the specific polymer or binder has different diffusivity or affinity to assure delivery of the beneficial agents at different rates. Thus, in accordance with the invention, multiple beneficial agents can be released at rates appropriate for their activities and the prosthesis of the invention has multiple beneficial agents that elute off the prosthesis at desired rates.

For example, a cationic phosphorylcholine which has a higher affinity for anionic therapeutic agents can be blended and dispersed as a first beneficial agent and lipophilic phosphorylcholine can be blended with lipophilic drugs as the second beneficial agent to effect different release rates respectively.

As discussed in greater detail below, the beneficial agent(s) and hydration inhibitors can be applied to the medical device in one or more coating layers. For example, alternating layers may be used to control delivery of multiple beneficial agents. Beneficial agents can be applied to the medical device alone or in combination with a suitable hydration inhibitor. Coatings that are suitable for use in this invention include, but are not limited to, any biocompatible polymeric material having suitable mechanical properties and in which the beneficial agent(s) is substantially soluble.

Conventional coating techniques also may be utilized to coat the beneficial agent onto the surface of the prosthesis such as spraying, dipping or sputtering and still provide the desired effect if performed appropriately. With such techniques, it may be desirable or necessary to use known masking or extraction techniques to control the location and amount in which beneficial agent is loaded.

According to some embodiments of the present invention, the beneficial agent may be loaded directly onto a component (e.g., by pipetting) or alternatively, the beneficial agent is loaded onto a base material layer that is applied a surface of the component (e.g., dip loading). For example and not limitation, a base coating, such as a binder or suitable polymer, is applied to a selected surface of the interventional component. If desired, a pattern may be formed on a component surface. Beneficial agent is then applied directly to the pattern of the base material. Thus, in accordance with the invention, beneficial agent can be delivered at rates appropriate for the intended use or application.

Figure 5:
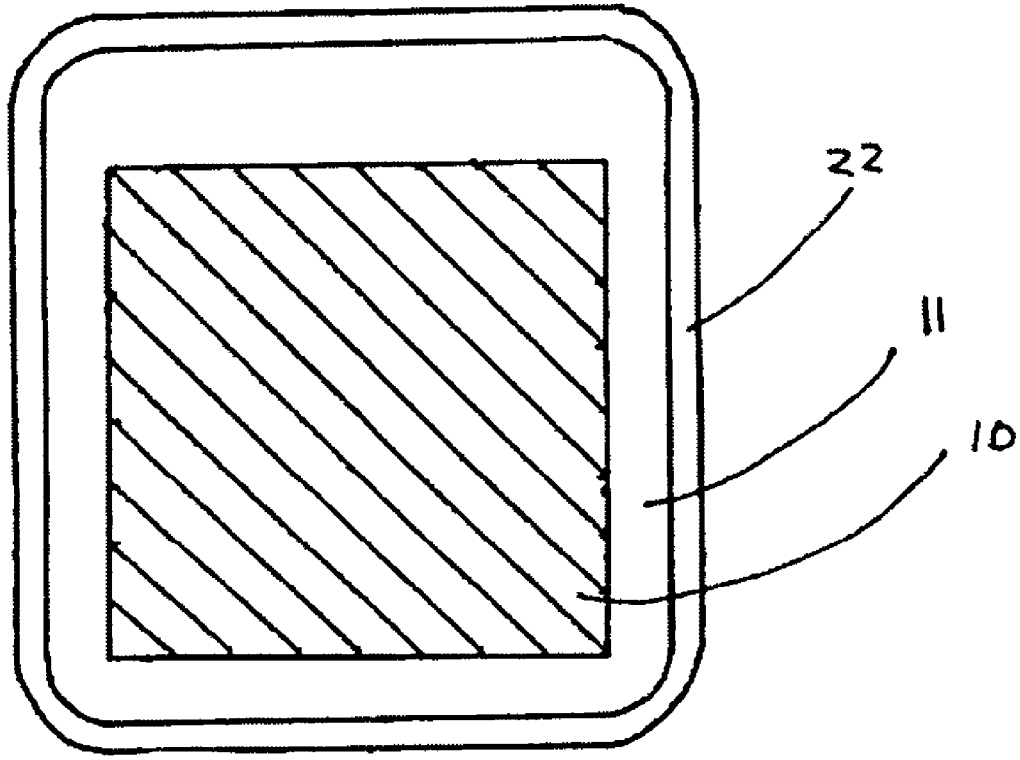
FIG. 5 is a cross-sectional view of a stent strut having a first layer of a beneficial agent and a second layer of a second beneficial agent acting as a hydration inhibitor.
Figure 6:
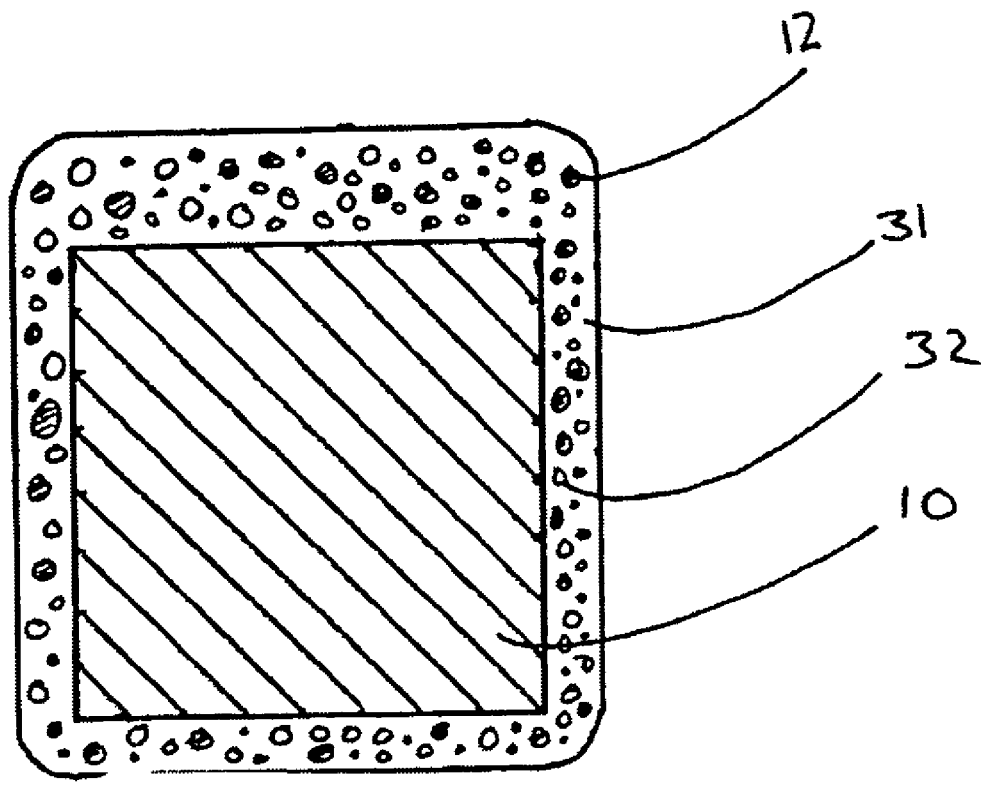
FIG. 6 is a cross-sectional view of a stent strut having a base layer of polymer material which is loaded with a mixture of a beneficial agent and a hydration inhibitor.
Figure 7:
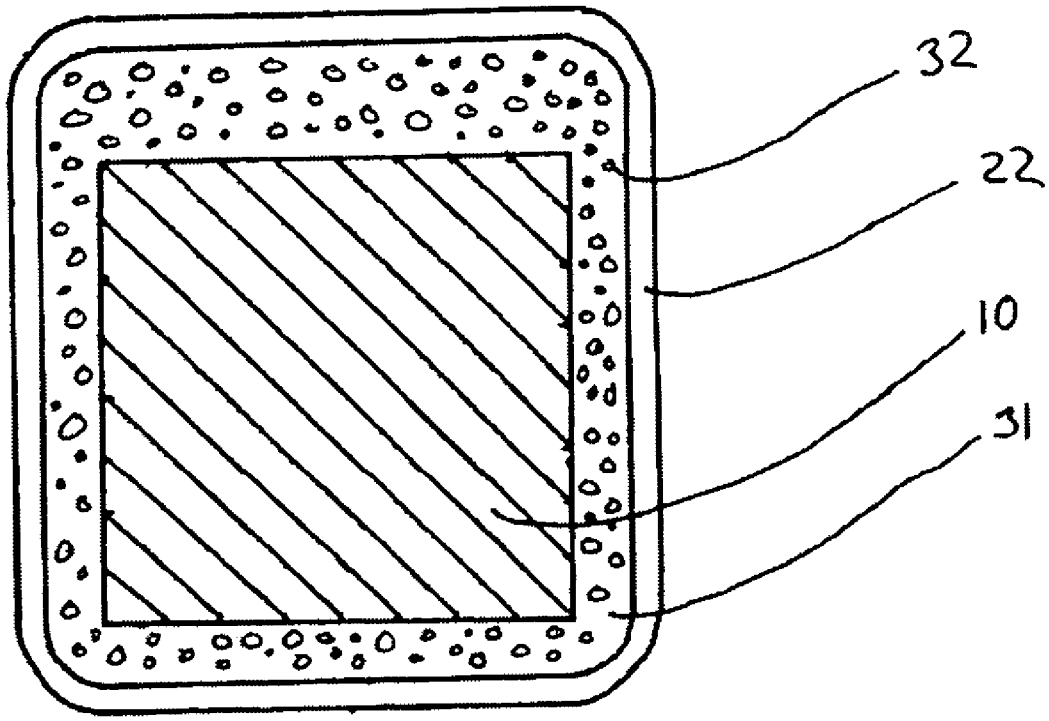
FIG. 7 is a cross-sectional view of a stent strut having a base layer of a polymer material which is loaded with a beneficial agent and a second layer of a second beneficial agent acting as a hydration inhibitor.

For purposes of explanation and illustration, and not limitation, exemplary embodiments of the interventional device in accordance with the invention are shown in FIGS. 1-7. In accordance with one aspect of the invention, as shown in FIG. 1, the interventional device is stent 5, having stent struts 10. In a preferred embodiment the interventional device in the form of a stent 5 has a base phosphorylchoine coating in which the beneficial drug is loaded. FIG. 3A shows a cross-sectional view of a vessel segment in which was placed a stent 5 coated with a PC polymer only, and FIG. 3B shows a cross-sectional view of a vessel segment in which was placed a stent 5 coated with a polymer plus drug. To further illustrate the different embodiments of the invention, a cross-sectional view of a stent strut 10 of the stent 5 of FIG. 1 is shown in FIGS. 4-7. In one embodiment of the invention, seen in FIG. 4, the stent strut 10 is loaded with a layer of beneficial agent 11 associated with a hydration inhibitor 12 as a mixture. As embodied herein, the mixture is loaded on the stent strut 10 thicker on one side for increased dosage if desired. In other embodiments not shown, however, the beneficial agent 11 and hydration inhibitor 12 can be loaded evenly throughout or selectively at desired locations on the surface of the interventional component. In a different embodiment of the invention as shown in FIG. 5, the stent strut 10 is loaded with a layer of beneficial agent 11, which is covered by a layer of a second beneficial agent acting as a hydration inhibitor 22. In yet another embodiment of the invention, shown in FIG. 6, the stent strut 10 has a base layer of a polymer material 31, preferably phosphorlycholine, wherein the polymer material is loaded with a beneficial agent 32 associated with a hydration inhibitor 12 as a mixture. FIG. 7 depicts yet another embodiment of the invention wherein a stent strut 10 has a base layer of polymer material 31 loaded with a beneficial agent 32, and a coating of a second beneficial agent acts as a hydration inhibitor 22 to control delivery of the first beneficial agent.

Figure 8:
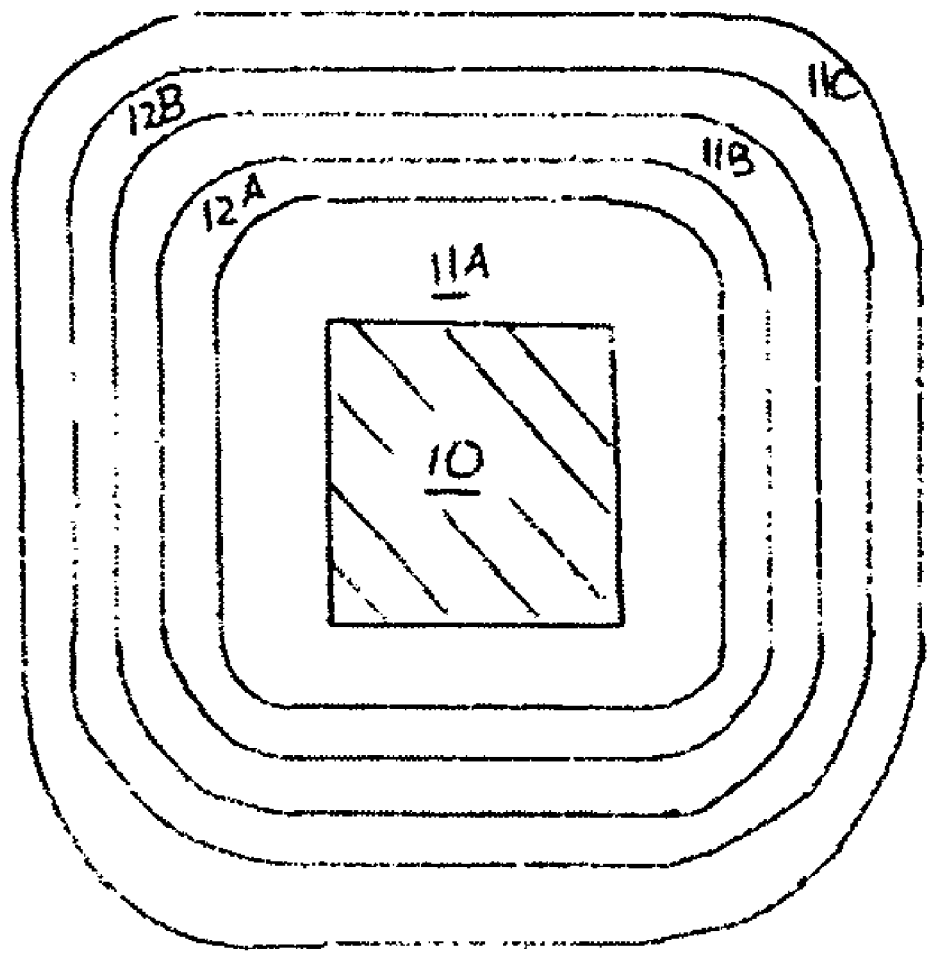
FIG. 8 is a cross sectional view of a stent strut having layers of a first beneficial agent alternating with layers of a second beneficial agent/hydration inhibitor.

Furthermore, in a different embodiment of the invention as seen in the cross sectional view of FIG. 8 a stent strut 10 has layers 11A, 11B and 11C of a first beneficial agent alternating with layers 12A and 12B of a second beneficial agent/hydration inhibitor. According to this embodiment, first beneficial agent, e.g., estradiol, from layer 11C elutes in an initial burst. Second beneficial agent/hydration inhibitor, e.g., ABT-578, in layer 12B controls elution of first beneficial agent from layer 11B. Thus, the Log P value of the second beneficial agent/hydration inhibitor is greater than the Log P value of the first beneficial agent, in accordance with principles of the present invention. Similarly, second beneficial agent/hydration inhibitor in layer 12A controls elution of first beneficial agent in layer 11A. Layers 12A and 12B enable midterm and late term delivery of first beneficial agent along with second beneficial agent/hydration inhibitor. Depending on the beneficial agents selected, layers 11A, 11B, 11C, 12A and 12B may optionally contain a polymer carrier or binder or other additive to facilitate processing or retention of the beneficial agent on the interventional device.

As those skilled in the art will appreciate, many variations of this embodiment are possible, depending on the medical condition(s) being treated, number and identity of beneficial agents selected, desired order of delivery and other factors. For example, layers 11A, 11B and 11C need not contain the same beneficial agent. Each can contain a different beneficial agent or two can contain the same beneficial agent with the third containing another beneficial agent. Similarly, layers 12A and 12B need not contain the same beneficial agent. Although not shown here, even more complicated variations can be achieved by those skilled in the art using the principles disclosed herein. For example, it may be desirable to achieve a relatively early delivery of estradiol to treat surface monocytes and a delayed delivery of dexamethasone to treat tissue monocytes and macrophages.

In a preferred embodiment of the invention, the hydration inhibitor has a Log P value of greater than 4.5 units and the beneficial agent has a Log P value less than 3 units. In this manner, the hydration inhibitor acts as a water barrier for the less hydrophobic beneficial agent, thereby reducing the release rate of the beneficial agent. For example and not limitation, the less hydrophobic beneficial agent can be ABT 620 {1-Methyl-N-(3,4,5-trimethoxyphenyl)-1H-indole-5-sulfonamide}, ABT 627, ABT 518 {[S—(R*,R*)]—N-[1-(2,2-dimethyl-1,3-dioxol-4-yl)-2-[[4-[4-(trifluoro-methoxy)-phenoxy]phenyl] sulfonyl]ethyl]-N-hydroxyformamide}, dexamethasone and the like and the hydration inhibitor can be Fenofibrate, Tricor™ or 3S,6R,7E,9R,10R,12R,14S,15E, 17E,19E,21S,23S,26R,27R,34aS)-9,10,12,13,14,21,22,23, 24,25,26,27,32,33,34,34a-Hexadecahydro-9,27-dihydroxy-3-[(1R)-2-[(1S,3R,4R)-3-methoxy-4-tetrazol-1-yl) cyclohexyl]-1-methylethyl]-10,21-dimethoxy-6,8,12,14,20, 26-hexamethyl-23,27-epoxy-3H-pyrido[2,1-c][1,4] oxaazacyclohentriacontine-1,5,11,28,29(4H,6H,31H)-pentone; 23,27-Epoxy-3H-pyrido[2,1-c][1,4] oxaazacyclohentriacontine-1,5,11,28,29(4H,6H,31H)-pentone.

The intervention component can include at least one reservoir or cavity therein. In accordance with another aspect of the invention, one or more of the reservoirs or cavities is loaded with a more hydrophilic first beneficial agent and then a second more hydrophobic beneficial agent can be loaded onto the first beneficial agent within the cavity or reservoir in a manner as described above.

In another embodiment of the invention, the interventional device can comprise a third beneficial agent. The third beneficial agent can be any of the beneficial agents disclosed above. In a preferred embodiment the third beneficial agent covers the second beneficial agent, the third beneficial agent having a Log P value less than the second Log P for rapid release of the third beneficial agent. In this embodiment the third beneficial agent can be the same as the first, so the beneficial agent is released rapidly upon implantation followed by a controlled release of the beneficial agent.

The present invention also provides a method for manufacturing a medical device for controlled delivery of beneficial agent. This method comprises the steps of providing an interventional component to be deployed in a patient; loading a beneficial agent on the interventional component for delivery therefrom, the beneficial agent having a first Log P value; and associating an effective amount of a hydration inhibitor with the beneficial agent to control delivery of the beneficial agent from the interventional component, the hydration inhibitor having a second Log P value, the second Log P value being greater than the first Log P value.

A number of methods can be used to load the beneficial agent onto the surface of the interventional component to provide for a controlled local areal density of beneficial agent. For example, the interventional component can be constructed to include pores or reservoirs which are impregnated or filled with beneficial agent, alone or in combination with a hydration inhibitor. The pores can be sized or spaced apart to correspond to or limit the amount of beneficial agent contained therein in accordance with the desired local areal density pattern along the length of the interventional device, wherein larger pores or-more dense spacing would be provided in such portions intended to have a greater local areal density.

According to various embodiments of the invention, the beneficial agent can be loaded directly onto the interventional component or alternatively, the beneficial agent is loaded onto a base material layer that is applied to at least a portion of the interventional component. For example and not limitation, a base coating, such as a binder or suitable polymer, is applied to a selected surface of the interventional component such that a desired pattern is formed on the interventional component surface. Beneficial agent and hydration inhibitor is then applied directly to the pattern of the base material. Generally, "controlled areal density" is understood to mean a known or predetermined amount of beneficial agent or mixture of beneficial agent and hydration inhibitor, either by weight or volume, over a unit surface area of the interventional component. In one aspect of the invention, the desired pattern corresponds to the desired controlled local areal density. For example, a greater amount of base material layer is applied to portions of the interventional device intended to have a greater local areal density of beneficial agent, and a lesser amount of base material is applied to portions of the interventional device intended to have a lower local areal density of beneficial agent. In yet another embodiment of the present invention, the beneficial agent can be applied directly to the surface of the interventional component.

Conventional coating techniques also can be utilized to coat the beneficial agent onto the surface of the interventional component such as spraying, dipping or sputtering and still provide the desired effect if performed appropriately. With such techniques, it can be desirable or necessary to use known masking or extraction techniques to control the location and amount in which beneficial agent is loaded. See U.S. patent application Ser. No. 09/950,307, filed Sep. 10, 2001; U.S. Pat. Nos. 6,329,386 and 6,015,815; and U.S. Patent Provisional Application entitled, "Medical Device Having a Hydration Inhibitor," filed on Mar. 10, 2003, each of which is incorporated herein by reference.

In yet another aspect of the invention, the beneficial agent(s) described herein can be applied to an intervention component that has been coated with a polymeric compound. Incorporation of the compound or drug into the polymeric coating of the interventional component can be carried out by dipping the polymer-coated interventional component into a solution containing the compound or drug for a sufficient period of time (such as, for example, five minutes) and then drying the coated interventional component, preferably by means of air drying for a sufficient period of time (such as, for example, 30 minutes). The polymer-coated interventional component containing the compound or drug can then be delivered to the coronary vessel by deployment from a balloon catheter, for example.

In a preferred embodiment, the beneficial agent and hydration inhibitor is "printed" onto the surface of the interventional component by a fluid-dispenser having a dispensing element capable of dispensing beneficial agent in discrete droplets, wherein each droplet has a controlled trajectory. In particular, the beneficial agent or mixture is selectively dispensed from the dispensing element to a predetermined portion of the interventional component in a raster format along a dispensing path. Advantageously, fluid-jetting technology can be used to deposit materials, such as beneficial agents and hydration inhibitors, in controlled volumes onto a substrate at a controlled location. See U.S. Provisional Patent Application Nos. 60/424,575; 60/424,577; 60/424,607; 60/424,574; and 60/424,576, all filed Nov. 7, 2002, each is incorporated by reference herein.

Further in accordance with the invention, the first beneficial agent loaded onto the interventional component has a first local areal density and the second beneficial agent loaded onto the interventional component has a second local areal density. As used herein, "areal density" refers to the amount of beneficial agent per unit surface area of a selected portion of the interventional component. "Local areal density" refers to the dosage of beneficial agent per local surface area of the interventional component. The local areal density of the first beneficial agent and the local areal density of the second beneficial agent can be uniform across each respective portion to define stepped changes in local area density or can be varied across a selected portion of the interventional component to define gradients of local area density. Accordingly, a medical device is provided having an interventional component that is at least partially loaded with beneficial agent having a local areal density that is varied along a selected portion of the body of the interventional component.

In accordance with the invention, the local areal density can be varied by varying the relative rate in which beneficial agent is loaded to a selected location along the interventional component. To this end, the frequency in which the droplets of beneficial agent are applied along a unit length of the dispensing path to the interventional component is varied. Alternatively, the relative rate of loading beneficial agent can be varied by varying the relative movement between the dispensing element and the interventional component. Another alternative for varying the relative rate of loading beneficial agent is to vary the amount of beneficial agent per droplet dispensed from the dispensing element. Other alternatives for varying the local areal density of beneficial agent loaded onto the interventional component include mixing the beneficial agent with a binder and varying the ratio of beneficial agent to binder. Alternatively, the amount of the mixture of beneficial agent and binder that is applied to the interventional component can be varied to achieve a varied local areal density of beneficial agent. However, other methods of varying the local areal density of beneficial agent known in the art can be used.

In accordance with another embodiment of the invention, the first surface of the interventional component is defined by a plurality of interconnecting structural members. Accordingly, the first surface can include a first selected set of structural members, e.g., a connector member, and the second surface can include a second selected set of the structural members, e.g., a ring-shaped element extending around the circumference of the interventional component.

Another feature of the present invention includes applying a layer of base material on a selected portion of the interventional component described above. The beneficial agent or mixture with hydration inhibitor is loaded onto the base material layer according to the methods described above. The base material layer can define a pattern for loading the beneficial agent onto the interventional component.

The present invention will be further understood by the examples set forth below, which are provided for purpose of illustration and not limitation.

EXAMPLES

Example 1

Elution Experiments of Beneficial Agents

I. Coating the Coupon with PC1036

Prior to any experimentation, coated stainless steel coupons were prepared. These coupons were 316L electropolished stainless steel discs (10 mm diameter). This size was chosen because the surface area of one side of the coupon is similar to the surface area of a 15-mm open cell BiodivYsio stent. The coupon was prepared by scratching a mark on one side of the coupon, to indicate the side of the coupon that will not be coated, and then cleaned. The cleaning was a two-step process in which the coupons are sonicated for 3 minutes in dichloromethylene and 3 minutes in ethanol. The coupons were allowed to dry at room temperature. One side of the coupon was coated using a filtered 20-mg/mL solution of phosphoryl choline polymer PC1036 (product of Biocompatibles Ltd., Farnham, Surrey, UK) in ethanol. Twenty μL PC solution was placed onto the coupon using a gas tight glass syringe, ensuring that the entire surface was coated but not spilling over the sides of the coupon. The coupons were initially air dried and then cured at 70° C. for 16 hours. They were then sent for gamma irradiation at <25 KGy. The resulting PC coating thickness was close to that of the stent and thick enough to accommodate the desired loaded drug dose, as graphically represented in FIG. 9A-B. FIG. 9A-B is a top and side view of a coated stainless steel coupon 30, having a PC-coating 20 on a electropolished stainless steel disc.

II. Loading the Coupon with Drugs of Interest

In these experiments, beneficial agents were loaded onto coupons and elution profiles examined. In general, the procedure is as follows. Twelve PC-coated coupons were loaded with each drug. The solutions of the drugs were usually 5.0 mg/mL in 100% ethanol and were filtered with a 0.45 μm filter prior to use.

The coupons were weighed before loading with the drug solution. To load 100 μg of drug, 20 μL of solution was placed (e.g., pipetted) on the center of the PC coated side of the coupon. The coupon was placed in a vial for 30 minutes with the lid closed to allow the drug to penetrate the coating. The lid was removed and the coupon was allowed to dry for an additional 90 minutes. To ensure that the coupon was completely dry, the coupon was weighed, and after 15 minutes the coupon was weighed a third time. When two weightings of the coupon were the same, the coupon was considered dry. The loaded, dry coupons were stored in a refrigerator protected from light.

III. Extracting Drugs from the Coupon

For each drug, six coupons were used to evaluate the total amount of drug loaded by the above procedure. The coupons were immersed in 5 mL of 50% ethanol, 50% water solution and sonicated for 1 hour. The concentration of the drug in the extraction solution was analyzed by HPLC.

At the end of the elution experiments discussed below, the coupons were removed from the elution media and immersed in 5 mL of 50% ethanol, 50% water solution and sonicated for 1 hour. The concentration of the drug in these vials indicated the amount of the drug remaining in the coupons at the end of the elution experiments.

IV. Elution Process

Six coated coupons of each drug were used for the elution experiments. The coupons were individually placed, coating side up, in small metal cups to hold the coupon and to allow movement to a new vial at each time point. The coupons were usually placed in a vial containing 10 mL of pH 7.4 phosphate buffered saline. The vials were stored in an orbital shaker, with horizontal shaking of 100 rpm, at 37° C. for at least 30 minutes before insertion of a coupon to allow the solution to equilibrate at the desired temperature. At least nine different time points were observed as shown in Table 2. After the desired time had lapsed, the coupon holder was lifted and allowed to drain. It was then placed into a pre-warmed vial corresponding to the next time point. This procedure continued until the predetermined time had elapsed. At that point, the coupons went through a drug extraction step as outlined earlier. The amount of drug in the elution samples was determined by HPLC.

To illustrate the effect of a relatively less hydrophilic beneficial agent/hydration inhibitor on a relatively more hydrophilic beneficial agent (i.e., a combination drugs) several different loading procedures were investigated. In particular for ABT-578 and dexamethasone combination the following were investigated.

TABLE 2

One-Day Elution Study Time and Sample Size

| Sample Number | Elution Time (Days) | Elution Time (Hours) | Elution Volume (mL) |
|---|---|---|---|
| 1 | 0.003 | 0.08 (5 min) | 10 |
| 2 | 0.010 | 0.25 (15 min) | 10 |
| 3 | 0.021 | 0.50 (30 min) | 10 |
| 4 | 0.042 | 1 | 10 |
| 5 | 0.083 | 2 | 10 |
| 6 | 0.125 | 3 | 10 |
| 7 | 0.167 | 4 | 10 |
| 8 | 0.208 | 5 | 10 |
| 9 | 0.250 | 6 | 10 |

FIGS. 10, 11, 12, 13 and 14 illustrate the effect of a hydration inhibitor according to the invention of a relatively more hydrophilic beneficial agent. In FIGS. 10-13, the drugs were applied to coupons; in FIG. 14, stents were coated.

Figure 10:
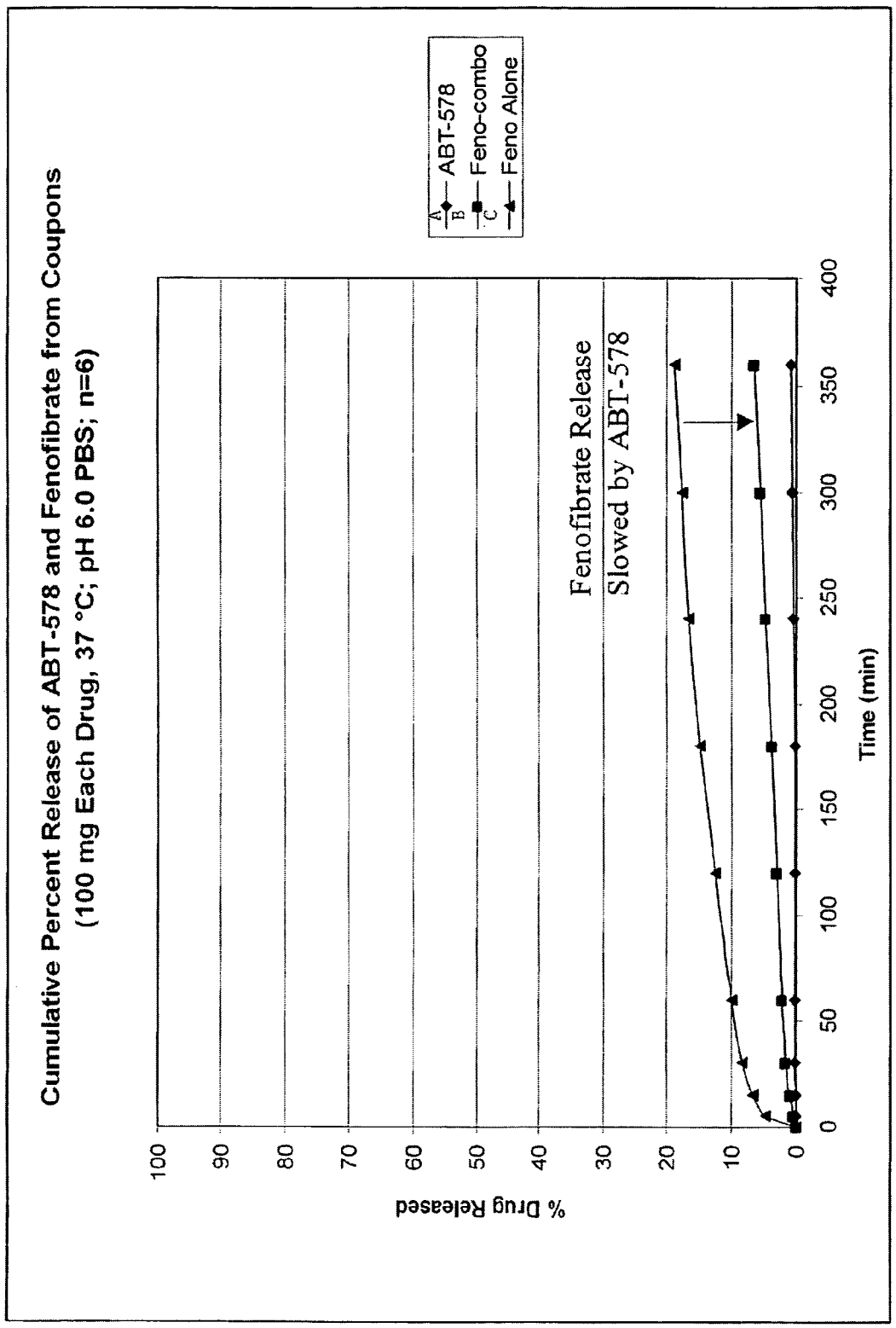
FIG. 10 is a graph showing the six-hour elution profile of the beneficial agent fenofibrate and the hydration inhibitor ABT-578.

In FIG. 10, the six-hour elution profile shown is where the beneficial agent is fenofibrate and the hydration inhibitor is ABT-578. Elution was carried out as described above. Curve A is the elution profile of ABT-578 alone. Curves B and C are the profiles for fenofibrate, in combination with ABT-578 and alone, respectively. Curve B shows that only about 7% of the fenofibrate was released from the coupon after 6 hours. As can be seen by comparing Curves B and C, the release of fenofibrate was significantly reduced by the presence of ABT-578.

Figure 11:
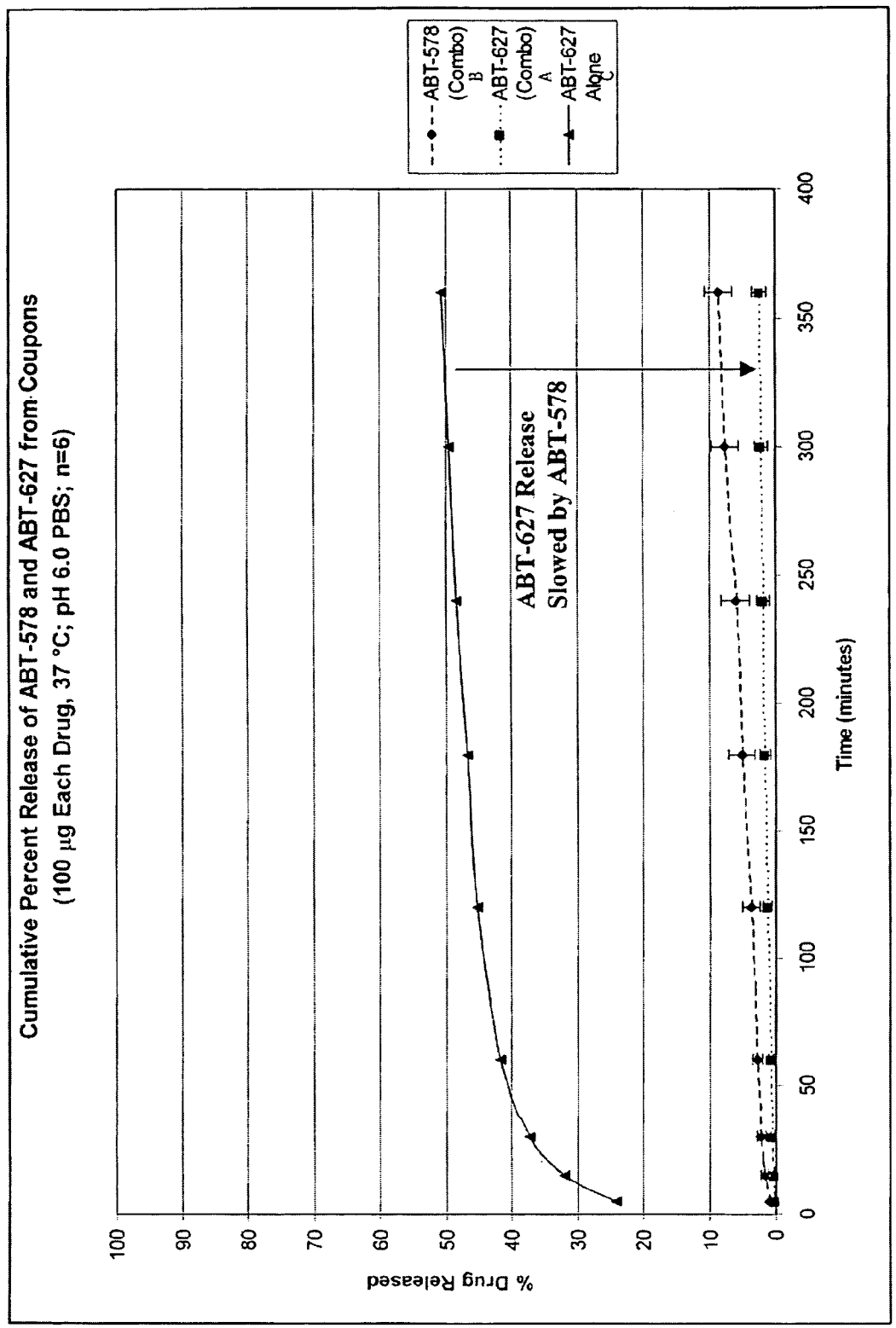
FIG. 11 is a graph showing the six-hour elution profile of beneficial agent ABT-627 (atrasentan) in the presence of hydration inhibitor ABT-578.

FIG. 11 illustrates the six-hour elution profile of beneficial agent ABT-627 (astrasentan) in the presence of hydration inhibitor ABT-578. Curves A and C are the elution profiles of ABT-627, in the presence of ABT-578 and alone, respectively. Curve B shows the elution of ABT-578 under the same conditions. Comparing Curves A and C, it is seen that the elution rate of relatively more hydrophilic ABT-627 is reduced in the presence of relatively less hydrophilic ABT-578. After six hours, much less than 10% of ABT-627 was released in the presence of ABT-578 (Curve C), compared to 50% in the absence of ABT-578 (Curve A).

Figure 12:
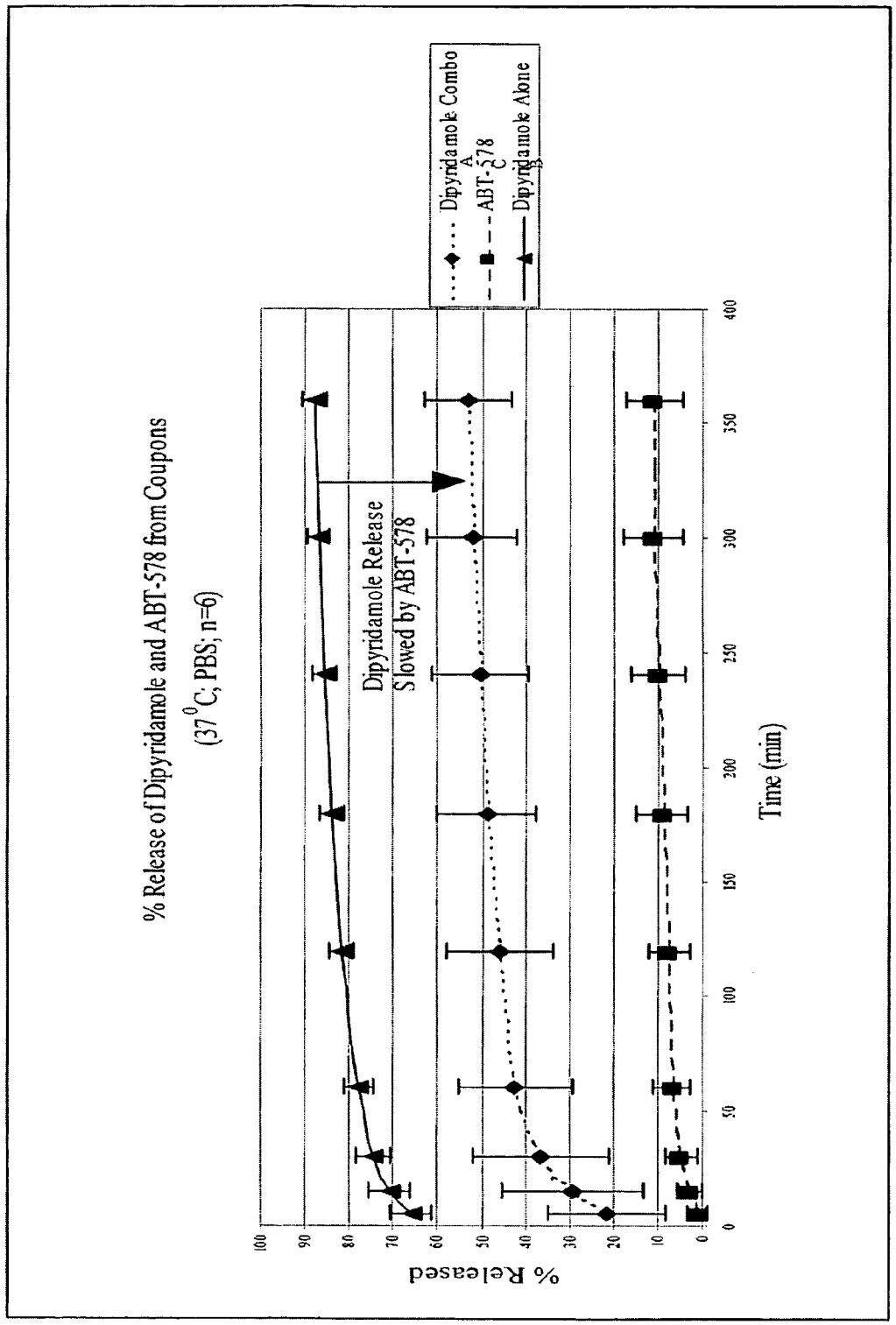
FIG. 12 is a graph showing the six-hour elution profile of beneficial agent dipyridamole in the presence of hydration inhibitor ABT-578.

FIG. 12 illustrates the six-hour elution profile of beneficial agent dipyridamole in the presence of hydration inhibitor ABT-578. Curves A and B are the elution profiles of dipyridamole, in the presence of ABT-578 and alone, respectively. Curve C shows the elution profile of ABT 578 under the same conditions. As can be seen by comparing Curves A and B, the amount of dipyridamole released from the coupons coated with ABT-578 and dipyridamole is only about 52% after six hours, compared to nearly 90% in the absence of ABT-578.

Figure 13:
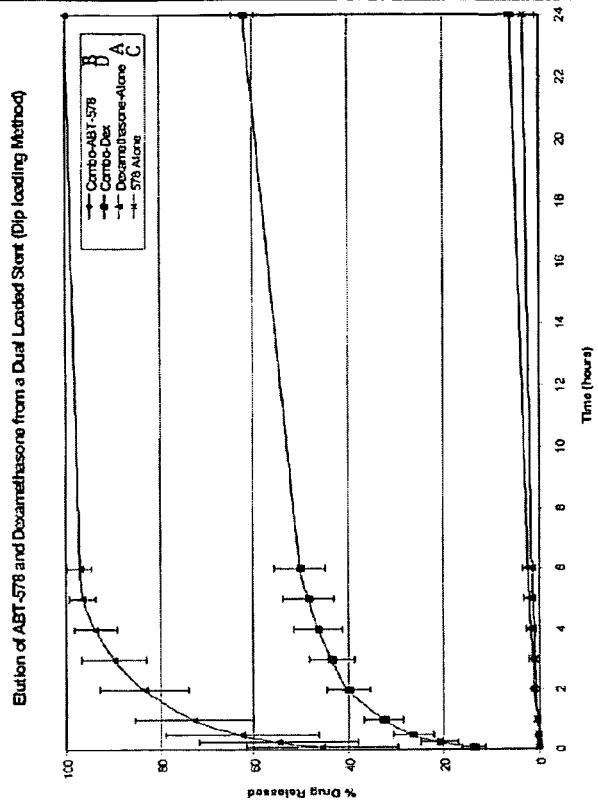
FIG. 13 is a graph showing the six hour elution profiles of beneficial agent dexamethasone in the presence of hydration inhibitor ABT-578.

FIG. 13 illustrates the six-hour elution profiles of beneficial agent dexamethasone in the presence of hydration inhibitor ABT-578. Curves A and B are the elution profiles of dexamethasone, alone and in the presence of ABT-578, respectively. Curves C and D (superimposed) are the elution profiles for ABT-578, alone and in the presence of dexamethasone, respectively, under the same conditions. As can be seen by comparing Curves A and B, the amount of dexamethasone remaining on the coupon containing dexamethasone and ABT-578 was nearly 70% compared to only 25% on the coupon on which no ABT-578 was present.

Figure 14:
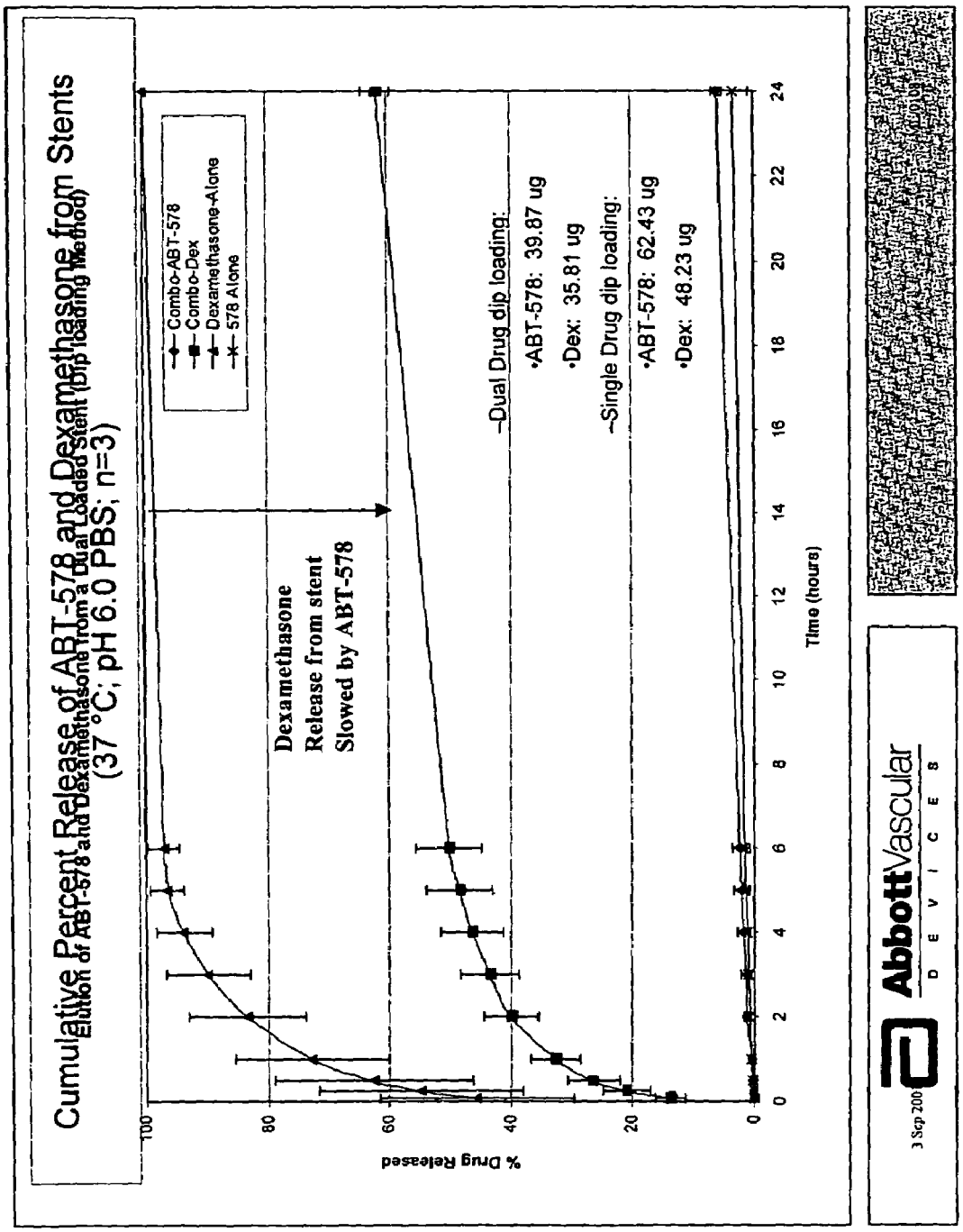
FIG. 14 is a graph showing the six-hour elution profile of beneficial agent dexamethasone in the presence of hydration inhibitor ABT-578 on a PC-coated stent.

FIG. 14 illustrates the six-hour elution profile of beneficial agent dexamethasone in the presence of hydration inhibitor ABT-578 on a PC-coated stent. Loading was accomplished by dip loading, that I,s a stent was dipped into a solution containing either one or both drugs and then permitted to dry. Curves A and B are the elution profiles for dexamethasone in the presence of ABT-578 and alone, respectively. Curves C and D are the elution profiles for ABT-578 in the presence of dexamethasone and alone, respectively. As can be seen by comparing Curves A and B, after 24 hours, almost no dexamethasone was released from the stent containing ABT-578 and dexamethasone, though about 40% of the dexamethasone was released from the stent having no ABT-578 present in the coating.

Example 2

Elution Experiments of Dexamethasone from Stents

I. Coating the Stents with PC1036

Prior to any experimentation, coated stents were prepared. These were 3.0 mm×15 mm 316L electropolished stainless steel stents. Each stent was spray coated using a filtered 20-mg/mL solution of phosphoryl choline polymer PC1036 (product of Biocompatibles Ltd., Farnham, Surrey, UK) in ethanol. The stents were initially air dried and then cured at 70° C. for 16 hours. They were then sent for gamma irradiation at <25 KGy.

II. Loading the Stents with Drugs of Interest

In these experiments, beneficial agents were loaded onto stents and elution profiles examined. In general, the procedure was as follows. Multiple PC-coated stents were loaded with each drug combination solution. The solutions of the drugs were usually in the range of 2-20 mg/mL of ABT-578 and 10.0 mg/mL dexamethasone in 100% ethanol, with ~10% PC1036 added to the solution to enhance film formation.

The stents were weighed before loading with the drug solution. To load approximately 10 μg/mL of each drug, a solution with equal amounts of ABT-578 and dexamethasone was sprayed onto the stent in a controlled fashion. The stent was allowed to dry before the stents were re-weighted to determine total drug load. The loaded, dry stents were stored in a refrigerator and were protected from light.

III. Extracting Drugs from the Stent

For each drug, 3 stents were used to evaluate the total amount of drug loaded by the above procedure. The stents were immersed in 6 mL of 50% ethanol, 50% water solution and sonicated for 20 minutes. The concentration of the drug in the extraction solution was analyzed by HPLC.

At the end of the accelerated elution experiments discussed below, the stents were removed from the dissolution media and immersed in 5 mL of 50% ethanol, 50% water solution and sonicated for 20 minutes. The concentration of the drug in these vials indicated the amount of the drug remaining on the stents at the end of the accelerated elution experiments. In this way, drug extraction was measured.

IV. Accelerated Elution Process

An HPLC method was developed for the determination of the amount of ABT-578 and dexamethasone eluted from phosphorylcholine (PC) coated metal stents (described above) in dissolution studies using an aqueous solution of polyethylene glycol 660 buffered at pH 4 as the dissolution medium. The method is used to determine the amount of drug that has eluted from the stent into the dissolution medium at 37° C. at selected time points, typically in a 24-hour period. This rapid, in vitro elution test is intended for use as a quality check on the manufacturing process and a fast reliable research tool for understanding the factors controlling elution of drugs from stents.

Two coated stents of each drug combination ratio were used for the accelerated elution experiments. The stents were individually dropped into the 1 liter containers of the dissolution bath apparatus containing 500 mL of dissolution medium at 37° C. The dissolution bath stirring paddles operated at 50 rpm. An autosampler was programmed to pull samples at multiple time points (Table 4). This procedure continued until the predetermined time had elapsed. At that point, the stent went through a drug extraction step as outlined earlier. The amount of drug in the elution samples was determined by HPLC.

To illustrate the effect of a relatively less hydrophilic beneficial agent/hydration inhibitor on a relatively more hydrophilic beneficial agent (i.e., a combination drugs) several different loading ratios were investigated. In particular, for ABT-578/dexamethasone (ABT-578/dex") combinations, the following were investigated at the ratios and loading solution concentrations set forth in Table 3, below.

TABLE 3

Loading Solution Ratios

| Solution Ratio ABT578: Dex | Concentration Dexamethasone | Concentration ABT578 | Concentration PC1036 | Number of Stents |
|---|---|---|---|---|
| 1:2 | 10 mg/ml | 20 mg/ml | 3 mg/ml | 6 |
| 1:1 | 10 mg/ml | 10 mg/ml | 2 mg/ml | 6 |
| 4:3 | 10 mg/ml | 7.5 mg/ml | 1.75 mg/ml | 6 |
| 2:1 | 10 mg/ml | 5 mg/ml | 1.5 mg/ml | 6 |
| 5:1 | 10 mg/ml | 2 mg/ml | 1.2 mg/ml | 6 |

TABLE 4

One-Day Accelerated Elution Study Time Points

| Data Point | Time Points (minutes) |
|---|---|
| 1 | 5 |
| 2 | 10 |
| 3 | 15 |
| 4 | 30 |
| 5 | 45 |
| 6 | 60 |
| 7 | 90 |
| 8 | 120 |
| 9 | 150 |
| 10 | 180 |
| 11 | 240 |
| 12 | 300 |
| 13 | 360 |
| 14 | 420 |
| 15 | 480 |
| 16 | 720 |
| 17 | 960 |
| 18 | 1200 |
| 19 | 1440 |

Figure 15:
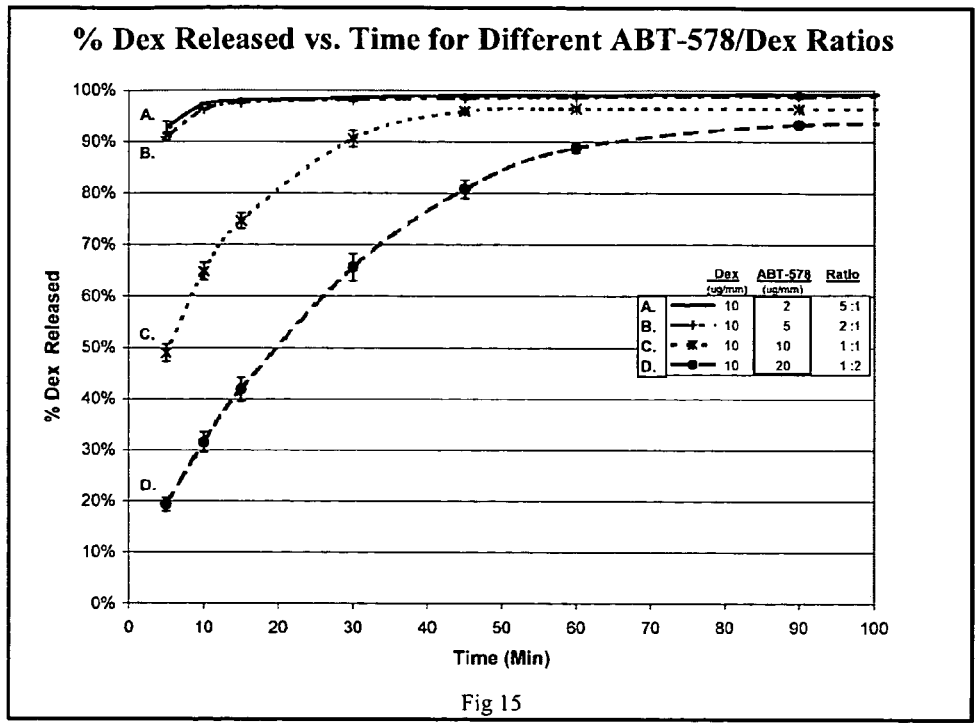
FIG. 15 is a graph showing the accelerated elution profiles of beneficial agent dexamethasone in the presence of hydration inhibitor ABT-578 at different ABT-578-to-dexamethasone ratios.

FIG. 15 illustrates the effect of a hydration inhibitor according to the invention on the elution of a relatively more hydrophilic beneficial agent from, for example, a stent.

In particular, FIG. 15 illustrates accelerated elution profiles (generated for example, by the technique described above) of beneficial agent dexamethasone in the presence of hydration inhibitor ABT-578 at different ratios. Curves A and B are the accelerated elution profiles of dexamethasone. As can be seen from the table in the plot, the amount of dexamethasone is higher than ABT-578. Curves C and D show the accelerated elution profiles for dexamethasone. In these curves, the ratio of ABT578-to-dexamethasone increases to 1:1 and 2:1. As can be seen by comparing Curves A through D, dexamethasone elution becomes increasingly slow with increasing ABT-578 concentration. Thus, the amount of dexamethasone remaining on a ABT-578/dexamethasone coated stent increases as the ratio of ABT578-to-dexamethasone increases.

Thus ABT-578 acts as an elution inhibitor for the more hydrophilic dexamethasone, further supporting the conclusion that relatively less hydrophilic beneficial agents can act as hydration inhibitors of relatively more hydrophilic agents.

Example 3

Protection of Dexamethasone from Degradation by the Presence of ABT-578

I Dexamethasone/ABT-578/PC Coated Stents

In these experiments, beneficial agents were loaded onto stents and the stability of the two drugs was examined. In general, the procedure was as follows. Multiple PC-coated stents were loaded with each drug combination from solution. The solutions of the drugs were usually in the range of 2-20 mg/mL of ABT-578 and 10.0 mg/mL dexamethasone in 100% ethanol, with ~10% PC1036 added to the solution to enhance film formation.

The stents were weighed before loading with the drug solution. To load approximately 10 µg/mL of each drug, a solution with equal amounts of ABT-578 and dexamethasone was sprayed onto the stent in a controlled fashion. The stent was allowed to dry before the stents were re-weighed to determine total drug load. The loaded, dry stents were stored in a refrigerator and were protected from light.

II. ETO Sterilization of Stents

After drug loading, stents were crimped onto catheter balloons and packaged into medical product Tyvek pouches for ETO (ethylene oxide) sterilization. The ETO sterilization process is standard in the medical device industry to ensure product safety. The ETO process was performed in a high humidity, elevated temperature environment to ensure microbe and spore kill.

III. Extracting Drugs from the Stent

For each drug, multiple stents were used to evaluate the purity and stability of the drug loaded by the above procedure. The stents were immersed in 6 mL of 50% ethanol, 50% water solution and sonicated for 20 minutes. The concentration and the presence of degradant-related impurities of the drug in the extraction solution were analyzed by HPLC.

Figure 16:
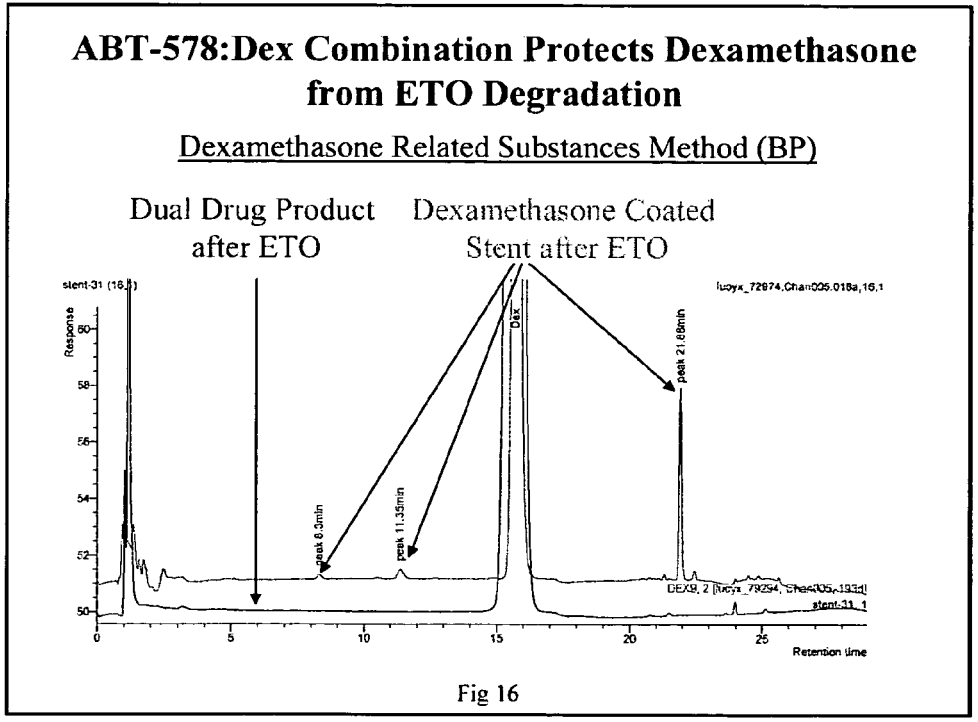
FIG. 16 shows the overlay of a chromatogram of a stent loaded with only dexamethasone and a chromatogram of a stent loaded with both dexamethasone and ABT-578 at a 1-to-1 ratio.

FIG. 16 shows the overlay of a chromatogram of a stent loaded with only dexamethasone and a chromatogram of a stent loaded with both dexamethasone and ABT-578 at a 1-to-1 ratio. As can be seen in the figure, dexamethasone in the dexamethasone-only coating degraded in the ETO sterilization environment with the production of at least three impurity peaks at 8.3, 11.3, and 21.8 minutes. In contrast, dexamethasone that was loaded in combination with ABT-578 in this same high humidity environment did not degrade. The impurity peaks seen in the dexamethasone-only coated stents were not present, nor were any impurity peaks evident in the chromatogram.

This figure thus demonstrates that ABT-578 acts a hydration inhibitor for the more hydrophilic dexamethasone, and that this inhibition has the effect of stabilizing the more hydrophilic drug dexamethasone in the presence of the less hydrophilic drug ABT-578.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and or methods of use of the invention, can be made without departing from the spirit and scope thereof.

What is claimed is:

1. A medical device comprising:
   an interventional component to be deployed in a patient;
   a beneficial agent to be delivered from the interventional component, the beneficial agent loaded on at least a portion of the interventional component and having a first Log P value; and
   an effective amount of a hydration inhibitor associated with the beneficial agent to control delivery of the beneficial agent from the interventional component, the hydration inhibitor having a second Log P value, the second Log P value being greater than the first Log P value, wherein the effective amount of the hydration inhibitor is an amount sufficient to shift the liquid-solid contact angle of the beneficial agent in association with the hydration inhibitor to at least 50 degrees.

2. The device according to claim 1, wherein the beneficial agent is selected from a group consisting of antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, pro-drugs and combinations thereof.

3. The device according to claim 2, wherein the beneficial agent is selected from the group of indomethacin, phenyl salicylate, B-estradiol, vinblastine, ABT-627, testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof.

4. The device according to claim 2, wherein the beneficial agent is a nucleic acid that encodes a pharmaceutically useful peptide or an anti-sense oligo-nucleotide used to control a gene of interest in a cell of the patient.

5. The device according to claim 1, wherein the hydration inhibitor is selected from a group consisting of beneficial agents, polymeric materials, markers, additives, and combinations thereof.

6. The device according to claim 1, wherein the hydration inhibitor is a second beneficial agent.

7. The device according to claim 6, wherein the second beneficial agent is selected from a group consisting of antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, radiopaque agents markers and combinations thereof.

8. The device according to claim 7, wherein the second beneficial agent is selected from a group consisting of paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, ABT-578, ABT-627 and analogs, derivatives, or combinations thereof.

9. The device according to claim 6, wherein the hydration inhibitor is associated with the first beneficial agent as a layer of the second beneficial agent at least partially covering the first beneficial agent.

10. The device according to claim 9, further comprising an outer layer of a third beneficial agent, the third beneficial agent having a third Log P value.

11. The device according to claim 10, wherein the third Log P value is less than the second Log P value.

12. The device according to claim 10, wherein the third beneficial agent is the same as the first beneficial agent.

13. The device according to claim 6, wherein the hydration inhibitor is associated with the first beneficial agent as a mixture of the second beneficial agent with the first beneficial agent.

14. The device according to claim 1, wherein the hydration inhibitor is associated with the beneficial agent as a mixture of the hydration inhibitor and the beneficial agent.

15. The device according to claim 14, wherein the hydration inhibitor is an additive.

16. The device according to claim 15, wherein the additive is selected from a group consisting of nitrophenyl octyl ether, bisethylhexyl sebacate, diisododecylphthalate, N-methylpyrrolidone, linolenic acid, linoleic acid, stearic acid, oleic acid, and combinations thereof.

17. The device according to claim 14, wherein the hydration inhibitor is a polymeric material.

18. The device according to claim 17, wherein the polymeric material is selected from a group consisting of phosphorylcholine, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane, polycarbonate urethanes, polyethylene, polyethylene terapthalate, ethylene vinyl acetate, ethylene vinyl alcohol, silicone polysiloxanes, substituted polysiloxanes, polyethylene oxide, polybutylene terepthalate-co-PEG, PCL-co-PEG, PLA-co-PEG, polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or combination thereof.

19. The device according to claim 14, wherein the polymeric material has a zwitterionic pendant group.

20. The device according to claim 1, further comprising a layer of polymeric material on at least a portion of a surface of the interventional component, the beneficial agent at least partially loaded onto the layer of polymeric material.

21. The device according to claim 20, wherein the layer of polymeric material has a zwitterionic pendant group.

22. The device according to claim 21, wherein the layer of polymeric material has a phosphoryl choline pendant group.

23. The device according to claim 20, wherein the hydration inhibitor controls delivery of the beneficial agent from the layer of polymeric material.

24. The device according to claim 1, wherein the interventional component is selected from the group consisting of a stent, graft, stent-graft, valve, filter, coil, staple, suture, guidewire, catheter, and catheter balloon.

25. The device according to claim 1, wherein the first Log P value is at least about 0.5 units less than the second Log P value.

26. A method of manufacturing a medical device, the method comprising the steps of:
providing an interventional component to be deployed in a patient;
loading a beneficial agent on the interventional component for delivery therefrom, the beneficial agent having a first Log P value; and
associating an effective amount of a hydration inhibitor with the beneficial agent to control delivery of the beneficial agent from the interventional component, the hydration inhibitor having a second Log P value, the second Log P value being greater than the first Log P value, wherein the effective amount of the hydration inhibitor is an amount sufficient to shift the liquid-solid contact angle of the beneficial agent in association with the hydration inhibitor to at least 50 degrees.

27. The method according to claim 26, wherein the beneficial agent loaded by the loading step is selected from a group consisting of antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, pro-drugs and combinations thereof.

28. The method according to claim 27, wherein the beneficial agent loaded by the loading step is a nucleic acid, wherein the nucleic acid encodes a pharmaceutically useful peptide or an anti-sense oligo-nucleotide used to control a gene of interest in a cell of the patient.

29. The method according to claim 27, wherein the beneficial agent loaded by the loading step is selected from a group consisting indomethacin, phenyl salicylate, B-estradiol, vinblastine, ABT-627, testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof.

30. The method according to claim 26, wherein the hydration inhibitor associated by the associating step is selected from a group consisting of beneficial agents, polymeric materials, markers, additives, and combinations thereof.

31. The method according to claim 26, wherein the hydration inhibitor associated by the associating step is a second beneficial agent.

32. The method according to claim 31, wherein the second beneficial agent is selected from a group consisting of antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, radiopaque agents markers and combinations thereof.

33. The method according to claim 32, wherein the second beneficial agent is selected from a group consisting of paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, ABT-578, ABT-627 and analogs, derivatives, or combinations thereof.

34. The method according to claim 26, wherein the associating step includes applying the second beneficial agent as a layer to at least partially cover the first beneficial agent.

35. The method according to claim 34, further comprising the step of applying a third layer of a third beneficial agent on at least a portion of the interventional component, the third beneficial agent having a third Log P value.

36. The method according to claim 35, wherein the third Log P value is greater than the second Log P value.

37. The method according to claim 35, wherein the third Log P value is the same as the first Log P value.

38. The method according to claim 34, wherein the associating step includes forming a mixture of the second beneficial agent with the first beneficial agent.

39. The method according to claim 26, wherein the associating step includes forming a mixture of the hydration inhibitor and the beneficial agent.

40. The method according to claim 39, wherein the hydration inhibitor associated by the associating step is an additive.

41. The method according to claim 40, wherein the additive is selected from a group consisting of nitrophenyl octyl ether, bisethylhexyl sebacate, diisododecylphthalate, N-methylpyrrolidone, linolenic acid, linoleic acid, stearic acid, oleic acid, and combinations thereof.

42. The method according to claim 39, wherein the hydration inhibitor associated by the association step is a polymeric material.

43. The method according to claim 42, wherein the polymeric material is selected from a group consisting of phosphorylcholine, polycaprolactone, poly-D,L-lactic acid, poly-L-lactic acid, poly(lactide-co-glycolide), poly (hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly (iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane, polycarbonate urethanes, polyethylene, polyethylene terapthalate, ethylene vinyl acetate, ethylene vinyl alcohol, silicone polysiloxanes, substituted polysiloxanes, polyethylene oxide, polybutylene terepthalate-co-PEG, PCL-co-PEG, PLA-co-PEG, polyacrylates, polyvinyl pyrrolidone, polyacrylamide, thermoplastic elastomers, polyolefin elastomers, EPDM rubbers, polyamide elastomers, biostable plastic, acrylic polymers, nylon, polyesters, epoxies and derivatives or combination thereof.

44. The method according to claim 42, wherein the polymeric material has a zwitterionic pendant group.

45. The method according to claim 26, further comprising the step of applying a layer of polymeric material on at least a portion of a surface of the interventional component, and further wherein the loading step includes loading the beneficial agent at least partially onto the layer of polymeric material.

46. The method according to claim 45, wherein the layer of polymeric material applied by the applying step has a zwitterionic pendant group.

47. The method according to claim 46, wherein the layer of polymeric material applied by the applying step has a phosphoryl choline pendant group.

48. The method according to claim 45, wherein the hydration inhibitor associated by the associating step controls delivery of the beneficial agent from the layer of polymeric material.

49. The method according to claim 26, wherein the interventional component is selected from the group consisting of a stent, graft, stent-graft, valve, filter, coil, staple, suture, guidewire, catheter, and catheter balloon.

50. The method according to claim 26, wherein the first Log P value of the beneficial agent loaded by the loading step is at least about 0.5 units less than the second Log P value of the hydration inhibitor associated by the associating step.

51. The method according to claim 26, wherein the liquid-solid contact angle of the beneficial agent in association with the hydration inhibitor is at least about 70°.

52. A medical device comprising:
an interventional component to be deployed in a patient;
a beneficial agent to be delivered from the interventional component, the beneficial agent loaded on at least a portion of the interventional component and having a first Log P value; and
an effective amount of a hydration inhibitor associated with the beneficial agent to enhance the stability of the moisture sensitive beneficial agent to be delivered from the interventional component, the hydration inhibitor having a second Log P value, the second Log P value being greater than the first Log P value, wherein the effective amount of the hydration inhibitor is an amount sufficient to shift the liquid-solid contact angle of the beneficial agent in association with the hydration inhibitor to at least 50 degrees.

53. The device according to claim 52, wherein the beneficial agent is selected from a group consisting of antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligionucleotides, cell permeation enhancers, pro-drugs and combinations thereof.

54. The device according to claim 53, wherein the beneficial agent is selected from the group of indomethacin, phenyl salicylate, β-estradiol, vinblastine, ABT-627, testosterone, progesterone, paclitaxel, cyclosporin A, vincristine, carvedilol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, iotrolan and pro-drugs, analogs, derivatives, or combinations thereof.

55. The device according to claim 53, wherein the beneficial agent is a nucleic acid that encodes a pharmaceutically useful peptide or an anti-sense oligo-nucleotide used to control a gene of interest in a cell of the patient.

56. The device according to claim 52, wherein the hydration inhibitor is selected from a group consisting of beneficial agents, polymeric materials, markers, additives, and combinations thereof.

57. The device according to claim 52, wherein the hydration inhibitor is a second beneficial agent.

58. The device according to claim 57, wherein the second beneficial agent is selected from a group consisting of antioxidants, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, viral vectors, nucleic acids, monoclonal antibodies, antisense compounds, oligonucleotides, cell permeation enhancers, radiopaque agents markers and combinations thereof.

59. The device according to claim 58, wherein the second beneficial agent is selected from a group consisting of paclitaxel, rapamycin, rapamycin derivatives, pimecrolimus, everolimus, fenofibrate, carvedilol, taxoteres, tacrolimus, butylated hydroxytoluene, butylated hydroxyanisole, vitamin E, danazol, probucol, tocopherols, tocotrienols, ABT-578, ABT-627 and analogs, derivatives, or combinations thereof.

* * * * *